(12) United States Patent
Del Soldato et al.

(10) Patent No.: US 7,465,803 B2
(45) Date of Patent: Dec. 16, 2008

(54) NITRODERIVATIVES AS DRUGS FOR DISEASES HAVING AN INFLAMMATORY BASIS

(75) Inventors: Piero Del Soldato, Monza (IT);
Francesca Benedini, Milan (IT);
Patrizia Antognazza, Milan (IT)

(73) Assignee: Nicox S.A., Sophia Antipolis (FR)

( * ) Notice: Subject to any disclaimer, the term of this patent is extended or adjusted under 35 U.S.C. 154(b) by 981 days.

(21) Appl. No.: 10/398,289

(22) PCT Filed: Oct. 9, 2001

(86) PCT No.: PCT/EP01/11664

§ 371 (c)(1),
(2), (4) Date: Apr. 10, 2003

(87) PCT Pub. No.: WO02/30866

PCT Pub. Date: Apr. 18, 2002

(65) Prior Publication Data

US 2004/0023933 A1 Feb. 5, 2004

(30) Foreign Application Priority Data

Oct. 12, 2000 (IT) .......................... MI2000A2202

(51) Int. Cl.
*C07D 211/70* (2006.01)
*C07D 213/55* (2006.01)
(52) U.S. Cl. ..................... 546/334; 546/335
(58) Field of Classification Search ................. 546/334, 546/335
See application file for complete search history.

(56) References Cited

U.S. PATENT DOCUMENTS

| 4,721,709 | A | 1/1988 | Seth et al. |
|---|---|---|---|
| 5,859,053 | A | 1/1999 | Lesur et al. |
| 5,861,426 | A | 1/1999 | Del Soldato et al. |
| 6,040,341 | A | 3/2000 | Del Soldato et al. |
| 6,297,260 | B1 * | 10/2001 | Bandarage et al. .......... 514/327 |
| 6,538,033 | B2 | 3/2003 | Bing |
| 2002/0187536 | A1 | 12/2002 | Kulkarni et al. |

FOREIGN PATENT DOCUMENTS

| EP | 0 722 434 A | 7/1996 |
|---|---|---|
| EP | 0 738 706 A1 | 10/1996 |
| WO | 94/04484 A1 | 3/1994 |
| WO | 94/12463 A1 | 6/1994 |
| WO | 95/09831 A1 | 4/1995 |
| WO | 95/30641 A1 | 11/1995 |
| WO | WO 96/34848 | 11/1996 |
| WO | WO 98/09948 A2 | 3/1998 |
| WO | 99/27912 A1 | 6/1999 |
| WO | 99/27913 A1 | 6/1999 |
| WO | 00 44705 A | 8/2000 |
| WO | 00 51988 A | 9/2000 |
| WO | 00 61541 A | 10/2000 |
| WO | WO 00/61537 A2 | 10/2000 |
| WO | 00/77838 A1 | 12/2000 |
| WO | 01 00563 A | 1/2001 |
| WO | 01 04082 A | 1/2001 |
| WO | 01 012584 A | 2/2001 |
| WO | 01/66087 A1 | 9/2001 |
| WO | 01/66088 A1 | 9/2001 |
| WO | 03/022249 A1 | 3/2003 |
| WO | 03/080029 A1 | 10/2003 |
| WO | 2004/026808 A1 | 4/2004 |

OTHER PUBLICATIONS

The W. Greene, "Protective groups in organic synthesis," Harvard University Press, 1980.
Remington's Pharmaceutical Sciences, 15th Ed., 1975.
"Synthesis and Stability of 2-Methyl-2,4-diaza- and 2-Methyl-2,5-diaza-indene + (2-Methyl-pyrrolo[3,4-b] pyridine and -pyrrolo[3,4-c]pyridine)," J. Chem. Soc., Perkin Trans. 1, 1972, vol. 20, pp. 2485-2490.
"A T cell-dependent experimental liver injury in mice induced by Concanavalin A.," Tiegs G., Hentshel J., A. Wendel, J. Clin. Invest., Jul. 1992, vol. 90, pp. 196-203.
"EGF receptor signaling enhances in vivo invasiveness of DU-145 human prostate carcinoma cells," Turner T., Chen, P., Goodly L. J., Wells A., Clinical & Experimental Metastasis 1996, vol. 14, No. 4, pp. 409-418.
Gordon L. Amidon et al., "A Theoretical Basis for a Biopharmaceutic Drug Classification: The Correlation of in Vitro Drug Product Dissolution and in Vivo Bioavailability," Pharmaceutical Research, vol. 12, No. 3, 1995, pp. 413-420.
Richard J. Bing et al., "The Pharmacology of a New Nitric Oxide Donor: B-NOD," Biochemical and Biophysical Research Communications 275, 2000, pp. 350-353.
Carmela De Santo et al., "Nitroaspirin corrects immune dysfunction in tumor-bearing hosts and promotes tumor eradication by cancer vaccination," PNAS, vol. 102, No. 11, Mar. 15, 2005, pp. 4185-4190.
F. Fabbri et al., "Pro-apoptotic effect of a nitric oxide-donating NSAID, NCX 4040, on bladder carcinoma cells," Apoptosis, vol. 10, No. 5, 2005, pp. 1095-1103.

(Continued)

*Primary Examiner*—Michael G. Hartley
*Assistant Examiner*—Shirley V Gembeh
(74) *Attorney, Agent, or Firm*—Arent Fox LLP

(57) ABSTRACT

Use for the treatment of diseases having an inflammatory basis of compounds or salts thereof, having the following general formula (I): $A-X_1-L-(W)_p-NO_2$ wherein A contains the radical of a drug, $X_1$ and W are bivalent radicals, p is an integer equal to 1 or 0, and L is a covalent bond, CO, oxygen, sulphur, or $NR_{1C}$ where $R_{1C}$ is H or a $C_1-C_5$ linear or branched alkyl.

3 Claims, No Drawings

OTHER PUBLICATIONS

Jianjun Gao et al., "In Vitro Metabolism of Nitric Oxide-Donating Aspirin: The Effect of Positional Isomerism," The Journal of Pharmacology and Experimental Therapeutics, vol. 312, No. 3, 2005, pp. 989-997.

Sandra Huguenin et al., "Nitrosulindac (NCX 1102): A New Nitric Oxide-Donating Non-Steroidal Anti-Inflammatory Drug (NO-NSAID), Inhibits Proliferation and Induces Apoptosis in Human Prostatic Epithelial Cell Lines," Wiley InterScience, Mar. 16, 2004, pp. 132-141.

Sandra Huguenin et al., "Evaluation of the antitumoral potential of different nitric oxide-donating non-steroidal anti-inflammatory drugs (NO-NSAIDs) on human urological tumor cell lines," Cancer Letters 218, 2005, pp. 163-170.

Sandra Huguenin et al., "Antiproliferative effect of nitrosulindac (NCX 1102), a new nitric oxide-donating non-steroidal anti-inflammatory drug, on human bladder cancinoma cell lines," Molecular Cancer Therapeutics, 2003, pp. 291-298.

Khosrow Kashfi et al., "Non-COX-2 targets and cancer: Expanding the molecular target repertoire of chemoprevention," Biochemical Pharmacology 70, 2005, pp. 969-986.

Khosrow Kashfi et al., "Positional Isomerism Markedly Affects the Growth Inhibition of Colon Cancer Cells by Nitric Oxide-Donating Aspirin in Vitro and in Vivo," The Journal of Pharmacology and Experimental Therapeutics, vol. 312, No. 3., 2005, pp. 978-988.

Khosrow Kashfi et al., "Nitric Oxide-Donating Nonsteroidal Anti-Inflammatory Drugs Inhibit the Growth of Various Cultured Human Cancer Cells: Evidence of a Tissue Type-Independent Effect," The Journal of Pharmacology and Experimental Therapeutics, vol. 303, No. 3, 2002, pp. 1273-1282.

Christian Lavagna et al., "Antiproliferative Effects of Nitrosulindac on Human Colon Adenocarcinoma Cell Lines," Biochemical and Biophysical Research Communications, vol. 284, No. 3, 2001, pp. 808-816.

Niharika Nath et al., "NO-donating aspirin inhibits the growth of leukemic Jurkat cells and modulates β-catenin expression," Biochemical and Biophysical Research Communications 326, 2005, pp. 93-99.

Niharika Nath et al., "Nitric oxide-donating aspirin inhibits β-catenin/T cell factor (TCF) signaling in SW480 colon cancer cells by disrupting the nuclear β-catenin-TCF association," PNAS, vol. 100, No. 22, Oct. 28, 2003, pp. 12584-12589.

B. Rigas et al., "NO-SAIDs and cancer: promising novel agents," Digestive and Liver Disease 35 (Suppl. 2), 2003, pp. S27-S34.

B. Rigas et al., "Is inhibition of cyclooxygenase required for the chemopreventive effect of NSAIDs in colon cancer? A model reconciling the current contradiction," Medical Hypotheses 54(2), 2000, pp. 210-215.

Basil Rigas et al., "NO-releasing NSAIDs and colon cancer chemoprevention: A promising novel approach (Review)," International Journal of Oncology 20, 2002, pp. 885-890.

Basil Rigas et al., "Nitric-oxide-donating NSAIDs as agent for cancer prevention," Trends in Molecular Medicine, vol. 10, No. 7, Jul. 2004, pp. 324-330.

Basil Rigas et al., "Cancer Prevention: A New Era beyond Cyclooxygenase-2," The Journal of Pharmacology and Experimental Therapeutics, vol. 314, No. 1, 2005, pp. 1-8.

Justine Sarah Royle et al., "Nitric Oxide Donating Nonsteroidal Anti-Inflammatory Drugs Induce Apoptosis in Human Prostate Cancer Cell Systems and Human Prostatic Stroma Via Caspase-3," The Journal of Urology, vol. 172, Jul. 2004, pp. 338-344.

Adam Spiegel et al., "NO-donating aspirin inhibits both the expression and catalytic activity of inducible nitric oxide synthase in HT-29 human colon cancer cells," Biochemical Pharmacology 70, 2005, pp. 993-1000.

Anna Tesei et al., "NCX 4016, a nitric oxide-releasing aspirin derivative, exhibits a significant antiproliferative effect and alters cell cycle progression in human colon adenocarcinoma cell lines," International Journal of Oncology 22, 2003, pp. 1297-1302.

Anna Tesei et al., "In vitro and in vivo evaluation of NCX 4040 cytotoxic activity in human colon cancer cell lines," Journal of Translational Medicine 2005, 3:7, pp. 1-12.

Jennie L. Williams et al., "Nitric Oxide-releasing Nonsteroidal Anti-inflammatory Drugs (NSAIDs) Alter the Kinetics of Human Colon Cancer Cell Lines More Effectively than Traditional NSAIDs: Implications for Colon Cancer Chemoprevention," Cancer Research 61, Apr. 15, 2001, pp. 3285-3289.

Jennie L. Williams et al., "NO-donating aspirin inhibits intestinal carcinogenesis in $Min(APC^{Min1+})$ mice," Biochemical and Biophysical Research Communications 313, 2004, pp. 784-788.

Jennie L. Williams et al., "Growth Inhibition of Human Colon Cancer Cells by Nitric Oxide (NO)-Donating Aspirin Is Associated with Cyclooxygenase-2 Induction and β-Catenin/T-Cell Factor Signaling, Nuclear Factor 78 B, and NO Synthase 2 Inhibition: Implications for Chemoprevention," Cancer Research 63, Nov. 15, 2003, pp. 7613-7618.

Raymond K. Yeh et al., "NO-donating nonsteroidal anti-inflammatory drugs (NSAIDs) inhibit colon cancer cell growth more potently than traditional NSAIDs: a general pharmacological property?" Biochemical Pharmacology 67, 2004, pp. 2197-2205.

Hiroshi Yuasa et al., "Application of Calcium Silicate for Medicinal Preparation. I. Solid Preparation Adsorbing an Oily Medicine to Calcium Silicate," Chem. Pharm. Bull. 42(11), Nov. 1994, pp. 2327-2331.

JP 48029783, Matsumoto et al., Abstract.

O. A. Al-Swayeh et al., "Nitroparacetamol exhibits anti-inflammatory and anti-nociceptive activity", British Journal of Pharmacolgy (2000) 130, pp. 1453-1456.

Adrian W. Bak et al., "Cyclooxygenase-Independent Chemoprevention With an Aspirin Derivative in a Rat Model of Colonic Adenocarcinoma", Life Sciences, vol. 62, No. 23, 1998, pp. PL 367-373.

Viviane Bertrand et al., "Role of tumour necrosis factor-α and inducible nitric oxide synthase in the prevention of nitro-flurbiprofen small intestine toxicity", European Journal of Pharmacology 356 (1998), pp. 245-253.

Gary L. Wenk et al., "Mechanisms to prevent the toxicity of chronic neuroinflammation on forebrain cholinergic neurons", European Journal of Pharmacology 402 (2000), pp. 77-85.

* cited by examiner

NITRODERIVATIVES AS DRUGS FOR DISEASES HAVING AN INFLAMMATORY BASIS

CROSS-REFERENCE TO RELATED APPLICATION

This application is a National Stage entry of International Application No. PCT/EP01/11664, filed Oct. 9, 2001, the entire specification claims and drawings of which are incorporated herewith by reference.

The present invention relates to compounds and the use thereof for diseases affecting the digestive apparatus, in particular the intestinal tract, specifically colites, gastrites, enterites, duodenites and hepatopathies of various nature (on a viral, immune, dismetabolic basis due to intoxications from drugs such as paracetamol and other analgesic, antibiotic, antitumoural, antidepressive drugs, etc., alcohol, etc.).

The digestive apparatus diseases are very diffused. While the therapy of the peptic ulcer has generally reached efficacy, the same cannot be said for other diseases affecting the digestive apparatus. For example it is known that yearly in the Unites States more than 25 million people suffer diseases affecting liver and gall-bladder and more than 26,000 people die owing to chronic hepatopathies and cirrhosis. Generally the therapeutical treatment is widely unsatisfatory. Among the compounds used for these treatments interferon α-2b can be mentioned, which allows the recovery in about 30-40% of the cases affected by chronic hepatitis B and 20-25% of those affected by chronic hepatitis C.

However the interruption of the treatment causes a recidivism in 50-80% of the patients. Only 10% of the cases of hepatitis B are satisfactory with interferon α-2b. Another compound used for these pathologies is ribavirin, however the efficacy is not yet well known. Other used compounds are vaccines, which however are used only in the prophylaxis.

For the cirrhosis treatment there are generally no effective compounds. At present the treatment is above all of support and it can consist in a suitable diet, alcohol abstinence or in the administering of diuretics or vitamins.

The therapeutic treatment is generally unsatisfactory for the diseases affecting the intestinal tract such colites, duodenites, enterites. For example the therapy with 5-amino salicylic acid and derivatives thereof is not fully effective. The use of steroidal compounds (for example prednisolone and the like) can cause toxic symptoms or serious side effects.

It must be added that generally the pathologies on an inflammatory basis, such as those above described affecting the digestive apparatus, are considered precancerous forms, since they can evolve into tumoural processes. In the same way for the pathologies on an inflammatory basis, which can concern different systems such the urogenital, respiratory apparatuses, the skin districts, etc.

Therefore the treatment of these pathologies of inflammatory nature has a critical importance also in the prevention and in the treatment of tumoral diseases.

The need was felt to have available compounds active in diseases on an inflammatory basis, in particular those affecting the digestive apparatus and for the prevention and/or treatment of the tumoral processes related to the above diseases.

It has been surprisingly found by the Applicant that it is possible to solve the above technical problem with specific nitroderivatives as described hereunder.

An object of the present invention is the use, for diseases on an inflammatory basis, of nitroderivatives or salts thereof having the following general formula (I):

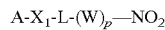

wherein:
  is an integer equal to 1 or 0;
  A=R-T$_1$-, wherein
    R is the radical of a precursor drug and it has the following formulas:

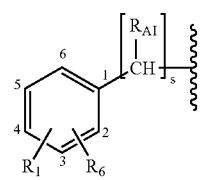

s is an integer and is 1 or 0;
  R$_{AI}$ is H, CH$_3$;
  R$_1$ is OCOR$_3$, R$_3$ being a C$_1$-C$_5$ linear or branched radical, NHCOR$_3$, wherein R$_3$ has the above meaning, or R$_1$ is OH, CH$_2$CH(CH$_3$)$_2$, phenyl, benzoyl, 4,6-dichlorophenylamino;
  R$_6$ is H, or an halogen atom, preferably fluorine;
  or R$_1$ and R$_6$, when are located in the adjacent positions 4 and 5 of the aromatic ring of formula (AI), form the radical of following formula (AIa):

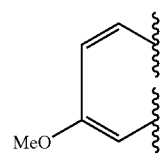

or R can be the following formula:

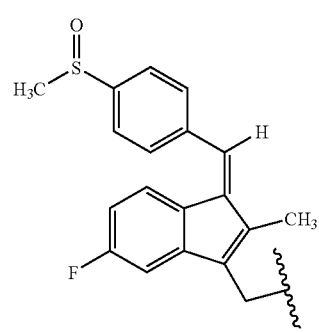

T$_1$=(CO)$_t$ or (X)$_{t'}$, wherein X=O, S, NR$_{1C}$, R$_{1C}$ is H or a linear or branched alkyl having from 1 to 5 carbon atoms, t and t' are integers and equal to zero or 1, with the proviso that t=1 when t'=0;
  t=0 when t'=1;
  X$_1$=-T$_B$-Y-T$_{BI}$- wherein
    T$_B$ and T$_{BI}$ are equal or different;
    T$_B$=(CO) when t=0, T$_B$=X when t'=0, X being as above;

$T_{BI}=(CO)_{tx}$ or $(X)_{txx}$, wherein tx and txx have the 0 or 1 value; with the proviso that tx=1 when txx=0; and tx=0 when txx=1; X is as above;

Y is a bivalent linking group selected from the following:

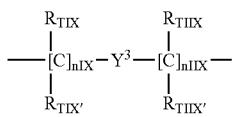
(II)

wherein:
nIX is an integer in the range 0-3, preferably 1;
nIIX is an integer in the range 1-3, preferably 1;
$R_{TIX}$, $R_{TIX'}$, $R_{TIIX}$, $R_{TIIX'}$, equal to or different from each other are H or a $C_1$-$C_4$ linear or branched alkyl; preferably $R_{TIX}$, $R_{TIX'}$, $R_{TIIX}$, $R_{TIIX'}$ are H;
$Y^3$ is a saturated, unsaturated or aromatic heterocyclic ring having 5 or 6 atoms, containing one or two nitrogen atoms,
an alkylene group R' wherein R' is a $C_1$-$C_{20}$ linear or branched when possible, preferably having from 2 to 6 carbon atoms, optionally substituted with one or more of the following groups: —NHCOR$_3$, wherein R$_3$ is as above, —NH$_2$, —OH or
a cycloalkylene having from 5 to 7 carbon atoms, optionally substituted with side chains R', R' being as above, one or more carbon atoms of the cycloalkylene ring can optionally be substituted by heteroatoms; or

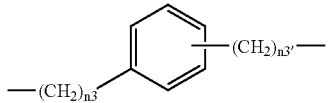
(III)

wherein n3 is an integer from 0 to 3 and n3' is an integer from 1 to 3;

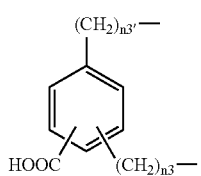
(IV)

wherein n3 and n3' have the above meaning,

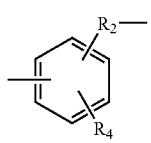
(V)

wherein
R$_4$ is hydroxy, hydrogen, R$_5$O— alkoxy wherein R$_5$ is a $C_1$-$C_{10}$ linear or branched or cyclic alkyl group, preferably R$_5$ is a methyl group;

R$_2$ is a $C_2$-$C_{10}$ linear or branched alkenylene group which can contain one or more double bonds, preferably R$_2$ is the ethenylene group (—CH=CH—); or

(VI)

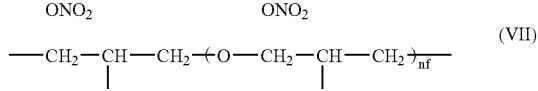
(VII)

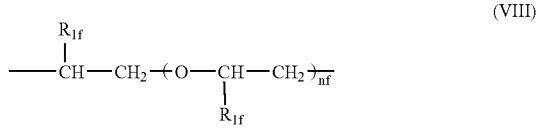
(VIII)

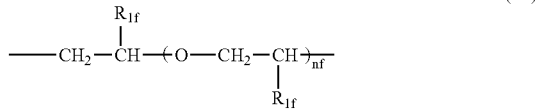
(IX)

wherein R$_{1f}$=H, CH$_3$ and nf is an integer from 0 to 6; preferably from 0 to 4;
L=covalent bond, or L=X, X being as above, or L=CO;
W=Y$_T$O wherein Y$_T$ has the same meanings of Y but in the compound of formula (I) Y$_T$ is equal to or different from Y. Preferably Y$_T$ is different from Y.

The diseases on an inflammatory basis are those particularly affecting the digestive apparatus, preferably the intestinal tract, such as for example colites, gastrites, enterites, duodenites; besides epatopathies and tumoral processes related to diseases on an inflammatory basis.

When in formula (AI), R$_1$ is an acetyloxy group in position 2 of the ring, s=0 and R$_6$=H and the free valence of the radical R is saturated with the —COOH group, the compound is known as Acetylsalicylic acid, when in formula (AI) R$_1$ is an hydroxyl group in position 2 of the ring, s=0 and R$_6$=H and the free valence of the radical R is saturated with a —COOH group, the compound is known as Salicylic Acid, when in formula (AI) R$_1$ is an acetylamino group in position 4 of the ring, s=0 and R$_6$=H and the free valence is saturated with an —OH group, the compound is known as Paracetamol, when in formula (AI) R$_1$ is CH$_2$CH(CH$_3$)$_2$ in position 4 of the ring, s=1, R$_{AI}$=CH$_3$ and R$_6$=H and the free valence is saturated with a —COOH group, the compound is known as Ibuprofen, when in formula (AI) R$_1$ is phenyl and it is in position 4 of the ring, s=1, R$_{AI}$=CH$_3$ and R$_6$=F in position 3 and the free valence is saturated with a —COOH group, the compound is known as Flurbiprofen, when in formula (AII) the free valence is saturated with the —COOH group, the compound is known as Sulindac;

when in formula (AI) R$_1$ and R$_6$ are the radical of formula (AIa) and they are connected with the positions 4 and 5 of the ring, s=1, R$_{AI}$=CH$_3$, R$_6$=H and the free valence is saturated with a —COOH group, the compound is known as Naproxen;

when in formula (AI) R$_1$ is a benzoyl radical in position 5 of the aromatic ring, s=1, R$_{AI}$=CH$_3$, R$_6$=H and the free valence is saturated with a —COOH group, the compound is known as Ketoprofen;

when in formula (AI) $R_1$=2,6-diclorofenilammino in position 2 of the ring, s=1, $R_{AI}$=H, $R_6$=H and the free valence is saturated with a —COOH group, the compound is known as Diclofenac.

Preferably $Y^3$ in formula (II) of the linking group Y of $X_1$ in formula (I) is selected from the following bivalent radicals:

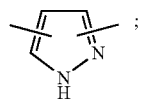 (Y1)

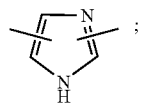 (Y2)

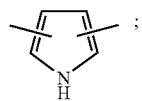 (Y3)

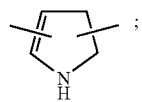 (Y4)

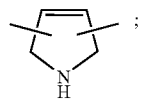 (Y5)

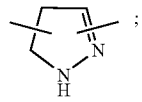 (Y6)

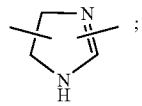 (Y7)

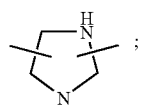 (Y8)

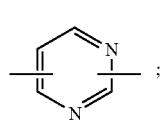 (Y9)

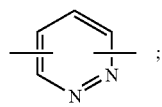 (Y10)

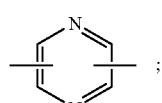 (Y11)

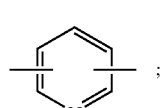 (Y12)

-continued

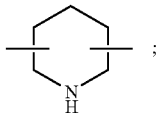 (Y13)

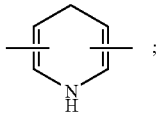 (Y14)

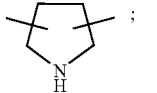 (Y15)

Preferably $Y^3$ is an aromatic ring having 6 atoms, containing one nitrogen atom, said aromatic ring having the two free valences respectively in the positions 2 and 6, or 2 and 3 or 2 and 5 with respect to the heteroatom.

The preferred of $Y^3$ is Y12 (pyridyl) substituted as above indicated. The bonds can also be in an unsymmetrical position, for example Y12 (pyridyl) can be substituted also in position 2 and 3; Y1 (pyrazol) can be 3,5-disubstituted.

The preferred compounds are those wherein in formula (I):
when in formula (AI) s=0 and $R_6$=H:
R is a radical of formula (AI) wherein the substituent $R_1$ is in position 2 of the aromatic ring, and it is selected between acetyloxy or hydroxyl, or it is an acetylamino group and then it is in position 4; -$T_1$-$T_B$- is a —CO—O— or —O—OC— ester group; Y of the radical $X_1$ is a bivalent linking group selected from the following:
a radical of formula (III) as above, wherein n3=0 and n3'=1,
a radical of formula (II) as above wherein $Y^3$ is Y12 as above defined,
a radical of formula (VIII) as above wherein $R_{1f}$ is hydrogen and nf=1;
$T_{B1}$=—O—, L=covalent bond; p=0;
R is a radical of formula (AI) wherein the substituent $R_1$ is in position 2 of the aromatic ring, and it is selected between acetyloxy or hydroxyl, or it is an acetylamino group and then it is in position 4; -$T_1$-$T_B$- is a —CO—O— or —O—OC— ester group; Y of the radical $X_1$ is a bivalent linking group having formula (V) as above wherein $R_4$ is a methoxyl group and $R_2$=—CH=CH—; -$T_{B1}$-L- is a —CO—O— or —O—OC— ester group; p=1; W=YO wherein Y is —(CH$_2$)$_4$— or —(CH$_2$)$_3$—;
R is a radical of formula (AI) wherein the substituent $R_1$ is in position 4 of the aromatic ring, and it is acetylamino; -$T_1$-$T_B$-=—O—CO—; Y of the radical $X_1$ is —(CH$_2$)$_3$—; -$T_{B1}$-L-=—O— (L=covalent bond); p=0;
R is a radical of formula (AI) wherein the substituent $R_1$ is in position 4 of the aromatic ring, and it is acetylamino; -$T_1$-$T_B$-=—O—CO—; Y of the radical $X_1$ is an ethylene group substituted with an acetylamino group: —CH(NHCOCH$_3$)—CH$_2$—; -$T_{B1}$-L-=—S—CO—; p=1; W=YO wherein Y is —(CH$_2$)$_3$—;
when in the formula (AI) s=1:
R is a radical of formula (AI), $R_6$=H or F in position 3 of the ring, $R_1$=CH$_2$CH(CH$_3$)$_2$ or phenyl in position 4, -$T_1$-$T_B$- is a —CO—O— ester group; Y of the radical $X_1$ is a bivalent linking group having formula (V) as above wherein R$_4$ is a methoxyl group and R$_2$=—CH=CH—; -T$_{B1}$-L- is a —CO—O— ester group; p=1; W=YO wherein Y is —(CH$_2$)$_3$—;

when in formula (I) R is a radical of formula (AII), -T$_1$-T$_B$-=—CO—O—; Y of the radical X$_1$ is a bivalent linking group selected from the following:

a radical of formula (II) as above wherein Y3 is Y12 as above,

—(CH$_2$)$_4$—;

-T$_{B1}$-=—O—, L=covalent bond; p=0.

The preferred compounds according to the present invention are those wherein:

the drug radical has formula (AI) and the compounds of formula (I) are the following:

2-(acetyloxy)benzoic acid 3-(nitrooxymethyl)phenyl ester,
2-(hydroxy)benzoic acid 3-(nitrooxymethyl)phenyl ester,
2-(acetyloxy)benzoic acid 4-(nitrooxymethyl)phenyl ester,
2-(hydroxy)benzoic acid 4-(nitrooxymethyl)phenyl ester,
2-(acetyloxy)benzoic acid 2-(nitrooxymethyl)phenyl ester,
2-(hydroxy)benzoic acid 2-(nitrooxymethyl)phenyl ester,
2-(acetyloxy)benzoic acid 6-(nitrooxymethyl)-2-methyl pyridinyl ester hydrochloride, or nitrate,
2-(hydroxy)benzoic acid 6-(nitrooxymethyl)-2-methyl pyridinyl ester hydrochloride, or nitrate,
2-(acetyloxy)benzoic acid 5-(nitrooxymethyl)-2-methyl pyridinyl ester hydrochloride, or nitrate,
2-(hydroxy)benzoic acid 5-(nitrooxymethyl)-2-methyl pyridinyl ester hydrochloride, or nitrate,
2-(acetyloxy)benzoic acid 3-(nitrooxymethyl)-2-methyl pyridinyl ester hydrochloride, or nitrate,
2-(hydroxy)benzoic acid 3-(nitrooxymethyl)-2-methyl pyridinyl ester hydrochloride, or nitrate,
trans-3-[4-[2-acetyloxybenzoyloxy]-3-methoxyphenyl]-2-propenoic acid 4-(nitrooxy)butyl ester,
trans-3-[4-[2-hydroxybenzoyloxy]-3-methoxyphenyl]-2-propenoic acid 4-(nitrooxy)butyl ester,
4-(nitrooxy)butanoic acid 4-(acetylamino)phenyl ester,
trans-3-[4-(4'-nitrooxybutyryloxy)-3-methoxyphenyl]-2-propenoic acid 4-(acetylamino)phenyl ester,
3-(nitrooxymethyl)-benzoic acid 4-(acetylamino)phenyl ester,
4-(nitrooxymethyl)-benzoic acid 4-(acetylamino)phenyl ester,
2-(nitrooxymethyl)-benzoic acid 4-(acetylamino)phenyl ester,
5-(nitrooxymethyl)pyridin-2-carboxylic acid 4-(acetyl amino)phenyl ester,
6-(nitrooxymethyl)-pyridin-2-carboxylic acid 4-(acetyl amino)phenyl ester,
3-(nitrooxymethyl)-pyridin-2-carboxylic acid 4-(acetylamino)phenyl ester,
5-(nitrooxymethyl)-pyridin-2-carboxylic acid 4-(acetylamino)phenyl ester,
5-(nitrooxymethyl)pyridin-2-acetic acid 4-(acetylamino)phenyl ester,
6-(nitrooxymethyl)pyridin-2-acetic acid 4-(acetylamino)phenyl ester,
3-(nitrooxymethyl)pyridin-2-acetic acid 4-(acetylamino)phenyl ester,
3-[(2-nitrooxy)ethyloxy]propanoic acid 4-(acetylamino)phenyl ester,
trans 3-[4-(4'-nitrooxybutyryloxy)-3-methoxy]phenyl-2-propenoic acid 4-(acetylamino)phenyl ester,
2-(acetylamino)-3-(4-nitrooxybutyryl)-3-mercaptopropanoic acid 4-(acetylamino)phenyl ester,
trans-3-[4-[α-methyl-4-(2-methylpropyl)phenylacetyloxy]-3-methoxyphenyl]-2-propenoic acid 4-nitrooxybutyl ester,
trans 3-[4-[2-fluoro-α-methyl(1,1'-biphenylyl)-acetyloxy]-3-methoxyphenyl]-2-propenoic acid 4-nitrooxybutyl ester,
(S) 6-metoxy-α-methyl-2-naphtalenacetic acid 2-methoxy-4-[(1E)-3-[4-(nitrooxy)butoxy]-3-oxo-1-propenyl]phenyl ester,
(S) 6-metoxy-α-methyl-2-naphtalenacetic acid 3-(nitrooxymethyl)phenyl ester,
(S) 6-metoxy-α-methyl-2-naphtalenacetic acid 6-(nitrooxymethyl)-2-methylpyridinil ester,
(S,S)—N-acetyl-S-(6-metoxy-α-methyl-2-naphtaleneacetyl) cysteine 4-(nitrooxy)butyl ester,
2-[(2,6-dichlorophenyl)amino]benzeneacetic acid 6-(nitro oxymethyl)-2-methylpyridinil ester chloridrate, The drug radical has formula AII and the compounds of formula (I) are the following:

(Z)-5-fluoro-2-methyl-1-[[4-(methylsulphinyl)phenyl]methylene]-1H-inden-3-acetic acid 4-(nitrooxy)butyl ester,
(Z)-5-fluoro-2-methyl-1-[[4-(methylsulphinyl)phenyl]methylene]-1H-inden-3-acetic acid 6-(nitrooxymethyl)-2-methylpyridinyl ester hydrocloride, or nitrate,
(Z)-5-fluoro-2-methyl-1-[[4-(methylsulphinyl)phenyl]methylene]-1H-inden-3-acetic acid 5-(nitrooxymethyl)-2-methylpyridinyl ester hydrocloride, or nitrate,
(Z)-5-fluoro-2-methyl-1-[[4-(methylsulphinyl)phenyl]methylene]-1H-inden-3-acetic acid 3-(nitrooxymethyl)-2-methylpyridinyl ester hydrocloride, or nitrate.

Other precursors of the general formula A=R-T$_1$- wherein the free valence is saturated with —OH, that can be used for obtaining the compounds of formula (I) are the following:

(S)-Benzenepropanoic acid, 4-[2-(2-benzoxazolylmethyl amino)ethoxy]-.-(2-ethoxy) of formula (XX):

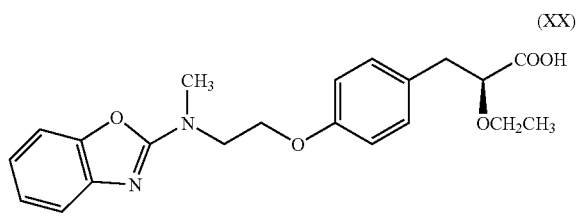

(S)-Benzenepropanoic acid, 4-[2-(2-benzoxazolylmethyl amino)ethoxy]-.-(2,2,2-trifluoroethoxy) of formula (XXI):

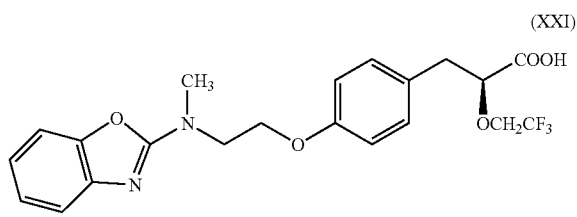

Compounds (XX) and (XXI) are described in PCT Patent Application WO 97/25042;

L-Tyrosine, N-(2-benzoylphenyl)-O-[2-(methyl-2-pyridinyl amino)ethyl] of formula (XXII):

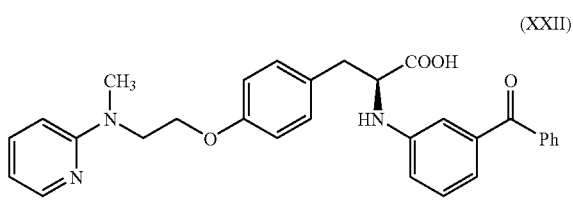

(XXII)

The above compound is described in PCT Patent Application WO 97/31907;

Prosta-5,9,12,14-tetraen-1-oic acid, 11-oxo-, (5Z,12E, 14E) (15-Deoxy Δ12,14-prostaglandin) of formula (XXIII):

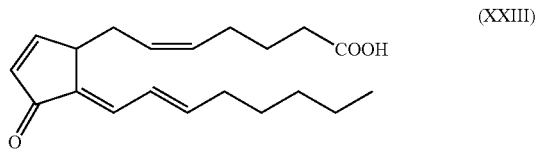

(XXIII)

(2S,5S)-4-(4-(4-carboxyphenyl)butyl)-2-heptyl-4-oxo-5-thiazolidine N,N-dibenzylacetamide of formula (XXIV):

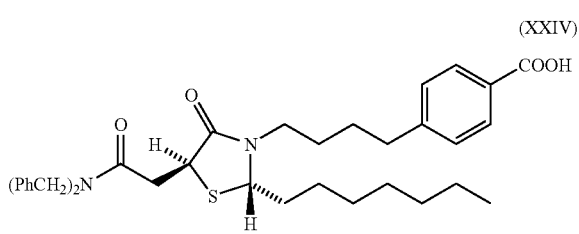

(XXIV)

The above compound is described in Proc. Natl. Acad. Sci 1999, 96(11), 6102-6106.

The bivalent radical precursors of formula (II) are for example those wherein the two free valences are saturated with two hydroxyl groups, or with one hydroxyl group and one carboxylic group. These compounds are available on the market.

When the drug radical R or the bivalent radical Y and/or W as above defined contain one or more asymmetric carbon atoms, the corresponding precursors can be used in the synthesis of the compounds of the invention both in racemic form and as single optical isomers.

When in the molecule of the compounds of the invention (formula I) a salifiable functional group, for example an amino or heterocyclic nitrogen is present, it is possible to use the corresponding salts. The latter are obtained by reaction in organic solvent such as for example acetonitrile, tetrahydrofuran, with an equimolecular amount of the corresponding organic or inorganic acid.

Examples of usable organic acids are the following: oxalic, tartaric, maleic, succinic, citric acid.

Examples of usable inorganic acids are the following: nitric, hydrochloric, sulphuric, phosphoric acid. Nitric and hydrochloric acid are preferred.

The compounds of the invention, as said, develop a marked protective action towards hepatopathies and in general towards diseases affecting the digestive apparatus, in particular the intestinal tract, in particular colites, gastrites, enterites, duodenites and hepatopathies. It has been found that the compounds of the invention in comparison with native precursors not only are not toxic as to the digestive apparatus, but unexpectedly they are able to prevent or reduce the diseases affecting this apparatus. For example the paracetamol efficacy as analgesic is known, however this compound causes damages at hepatic level (hepatic toxicity). The paracetamol nitrooxy derivatives according to the invention, besides being effective analgesic drugs, have no hepatic toxicity, but they are also able to prevent or reduce already existing hepatic damages.

The results obtained with the compounds of the invention are still more surprising if one considers that by using another NO donor such for example sodium nitroprussiate in pathologies affecting the digestive apparatus, there is no protection, on the contrary an hepatic damage occurs. Besides, this drug causes high hypotension.

As said, the compounds of the invention have a beneficial action also on tumoral processes, when used in the prophylaxis or in the therapy. As said, the pathologies on an inflammatory basis are considered precancerous forms, being able to subsequently evolve into tumoral processes. The pathologies on an inflammatory basis can involve various systems such as the urogenital, respiratory, skin, digestive system, etc.

Therefore the treatment of these pathologies of inflammatory nature has a critical importance also in the prevention and in the treatment of tumoral diseases.

In the treatment of tumoral diseases the compounds of the invention can be used alone or in combination with known antitumoral treatments, such for example the administering of chemotherapeutic drugs, for example cis-platinum, adriamycin etc., or the radiotherapeutic treatment.

It has unexpectedly been found by the Applicant that the compounds of the invention, when used in combination with the above tumoral treatments, synergically enhance the therapeutic effect.

The administering of the compounds of the invention can be made contemporaneously with the chemotherapeutic or radiotherapeutic treatments, or previously or subsequently to the chemotherapeutic or radiotherapeutic treatments.

Preferably the compounds of the invention are used for the treatment and/or prevention of the tumoral process affecting the digestive apparatus. The preferred compounds are the above ones.

The compounds of the invention are prepared according to known methods of the prior art.

In general if in the drug molecule or in the molecules of the radicals Y and W more reactive groups such as for example COOH and/or HX are present, they must be protected before the reaction according to the known procedures of the prior art; for example as described in the volume by Th. W. Greene: "Protective groups in organic synthesis", Harward University Press, 1980.

Acyl halides are prepared according to known procedures of the prior art, for example by thionyl or oxalyl chloride, halides of $P^{III}$ or $P^V$ in solvents inert under the reaction conditions, such for example toluene, chloroform, DMF, etc.

1) When in formula (I) L is a covalent bond and p=0, and the free valence of the drug radical R is saturated with a carboxylic group, the synthesis methods for obtaining the corresponding nitrooxyderivatives are the following:

1.a) The acyl halide of the drug of formula R—CO—Cl is reacted with an halogenalcohol of formula HO—Y-Hal, wherein Y is as above and Hal is halogen (Cl, Br, I).

R—COCl+HO—Y-Hal --------> R—CO—O—Y-Hal (1A)

1.b) Alternatively, the reaction can be carried out by reacting the sodium or potassium salt of the drug with a dihalogen derivative of general formula Y(Hal)$_2$, wherein Y and Hal are as above defined.

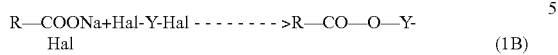 (1B)

1.c) Or the drug of formula RCOOH is treated with an agent activating the carboxyl selected from N,N'carbonyl diimidazol (CDI), N-hydroxybenzotriazole and dicyclohexylcarbodiimide in solvent such for example, DMF, THF, chloroform etc. at a temperature in the range −5° C.-50° C. and reacted in situ with a compound HO—Y-Hal, wherein Y and Hal are as above defined.

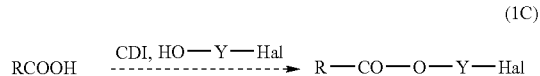 (1C)

1.d) Alternatively, the acyl halide of the drug is reacted with a compound HO—Y—OH, wherein Y is as above, in the presence of a base, in an organic solvent inert under the reaction conditions according to the scheme reported hereunder:

 (1D)

1.e) Alternatively to the previous syntheses the acyl halide of the drug is reacted with a compound HO-M-CHO, wherein M is an aromatic ring having 6 carbon atoms, or a radical Y$^3$ as above, in the presence of a base, in an organic solvent inert under the reaction conditions according to the scheme reported hereunder:

The obtained compound is subjected to hydrogenation in the presence of Palladium on carbon to give the corresponding alcohol:

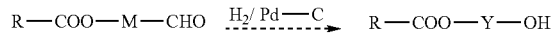

wherein Y is as above defined.

1.f) When the products obtained in the above reactions have formula R—COO—Y-Hal the corresponding nitrooxyderivatives are obtained by reacting the compound R—CO—O—Y-Hal with AgNO$_3$ in organic solvent such as acetonitrile, tetrahydrofuran according to the scheme:

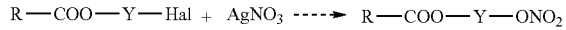

1.g) When the compounds obtained in the above reactions have formula R—COO—Y—OH the corresponding nitrooxyderivatives can be obtained by treatment with fuming nitric acid in organic solvent under anhydrous conditions and in inert atmosphere, in the presence of an inorganic acid different from the nitric acid, or with an organic acid, or of an anhydride of one or two organic acids.

1.h) Alternatively, in the compound of formula R—COO—Y—OH the hydroxyl group is subjected to halogenation, for example, with PBr$_3$, PCl$_5$, SOCl$_2$, PPh$_3$+I$_2$, and then reacted with AgNO$_3$ in organic solvent such as acetonitrile, tetrahydrofuran.

2) When in formula (I) L is a covalent bond and p=0, and the free valence of the radical R of the drug is saturated with a hydroxyl group, the synthesis methods for obtaining the corresponding nitrooxyderivatives are the following:

2.a) By reaction of the drug of formula R—OH with an acyl halide of formula Hal-Y—COHal, wherein Y and Hal are as above, according to the scheme:

 (2A)

2.b) By reaction of the drug of formula R—OH with an acyl halide of formula OH—Y—COHal, wherein Y and Hal are as above, according to the scheme:

 (2B)

2.c) When the compounds obtained in the above reactions have formula R—OCO—Y-Hal or R—OCO—Y—OH the corresponding nitrooxyderivatives are obtained as described in 1.f and 1.h respectively.

3) When in formula (I) p=1 and L=X, wherein X is as above, or L=CO, and the free valence of the radical R of the drug is saturated with a carboxylic group, the synthesis methods for obtaining the corresponding nitrooxyderivatives are the following:

3.a) By reaction between the acyl halide of the drug and the compound of formula HX—Y—COOH, wherein X and Y are as above defined, according to the known methods of the prior art, to give the compound R—CO—X—Y—COOH which is transformed into the corresponding sodium salt and reacted with a compound of formula Hal-Y$_T$—R$_8$ wherein Hal and Y$_T$ are as above and R$_8$ is Cl, Br, Iodine, OH:

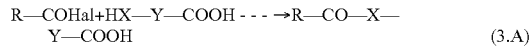 (3.A)

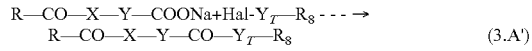 (3.A')

If R$_8$=OH the compound of formula (3.A') is subjected to halogenation as described in 1.h); if R$_8$=Hal the compound of formula (3.A') is reacted with AgNO$_3$ in organic solvent such as acetonitrile, tetrahydrofuran:

3.b) When Y$_T$ is a C$_4$ linear alkylene, the acid of formula (3.A) is reacted with triphenylphosphine in the presence of an halogenating agent such as CBr$_4$ or N-bromosuccinimide in tetrahydrofuran to give the compound of formula (3.A') wherein R$_8$=Br which is transformed into the corresponding nitrooxyderivative as described in 1.h.

4) When in formula (I) p=1 and L=X or CO, and the free valence or the radical R of the drug is saturated with an hydroxyl group, the synthesis methods for obtaining the corresponding nitrooxyderivatives are the following:

4.a) Reaction of the drug of formula R—OH with an acyl halide of formula HX—Y—COHal, wherein X and Y are as above defined, according to the known methods of the prior art, to give the compound R—O—CO—Y—XH which is reacted with a compound of formula $R_8$—$Y_T$—COHal wherein $R_8$ and $Y_T$ are as above.

R—OH+HX—Y—COCl - - - →R—O—CO—Y—XH (4.A)

R—O—CO—Y—XH+$R_8$—$Y_T$CO-Hal - - - → R—O—CO—Y—X—CO—$Y_T$—$R_8$ (4A')

4.b) Alternatively, the drug of formula R—OH is reacted with a compound of formula HX—Y—COOH, wherein X and Y are as above, in the presence of dicyclohexylcarbodiimide as described in 1.c, to give the compound R—O—CO—Y—XH, which is reacted with a compound of formula $R_8$—$Y_T$—COCl wherein $R_8$ and $Y_T$ are as above defined to give the following compound:

R—O—CO—Y—X—CO—$Y_T$—$R_8$ (4.B).

When $R_8$=OH the compound of formula (4.B) or of formula (4A') is subjected to halogenation as described in 1.h);
if $R_8$=Hal the compound of formula (4.B) is reacted with $AgNO_3$ in organic solvent such as acetonitrile, tetrahydrofuran.

The compounds of the present invention are formulated in the corresponding pharmaceutical compositions for parenteral, oral and topical use according to the well known techniques in the field, together with the usual excipients; see for example the volume "Remington's Pharmaceutical Sciences 15a Ed.".

The amount on a molar basis of the active principle in these formulations is the same, or lower, with respect to that used as antiinflammatory and/or analgesic drug of the corresponding precursor drug.

The daily administrable doses are those of the antiinflammatory and/or analgesic precursor drugs, or, in case, lower. The daily doses can be found in the literature of the field, such as for example in "Physician's Desk reference".

The following Examples illustrate the invention and they are not limitative of the scope of the same.

EXAMPLES

Example 1

Synthesis of 2-acetyloxybenzoic acid 6-(nitrooxymethyl)-2-methylpyridinyl ester hydrochloride of Formula A) Synthesis of 2,6-bis-(chloromethyl)pyridine To thionyl chloride (11.6 ml, 158 mmoles), cooled at 0° C., 2,6-bis-(hydroxymethyl)pyridine (4 g, 28 mmoles) is added very slowly. The obtained solution is left under stirring for 2 hours at room temperature, then the thionyl chloride in excess is evaporated at a reduced pressure. The obtained residue is treated with chloroform and it is evaporated again at a reduced pressure to remove the thionyl chloride residues. The raw product is treated with chloroform and washed with water. The organic phase is anhydrified with sodium sulphate and dried obtaining 4.81 g of the product as white solid having melting point=76-78° C.

B) Synthesis of 2-acetyloxybenzoic acid 6-(chloromethyl)-2-methylpyridinyl ester To a solution of acetylsalicylic acid (1.6 g, 8.88 mmoles) in N,N'-dimethylformamide (20 ml) and under stirring sodium ethylate (0.64 g, 8.88 mmoles) is added. After 30 minutes the obtained solution is added to a solution of 2,6-bis-(chloromethyl)pyridine (4.72 g, 26.81 mmoles) in N,N'-dimethylformamide (20 ml). The solution is left at room temperature for 7 days, under stirring, then it is diluted with ethyl ether and washed with water. The separated organic phases are anhydrified with sodium sulphate and the solvent is evaporated at a reduced pressure. The reaction raw product is purified by chromatography on silica gel eluting with n-hexane/ethyl acetate 7/3. 1.7 g of the product as yellow oil are obtained.
$^1$H—NMR (200 MHz)(CDCl$_3$): 8.10(1H,d); 7.74(1H,t); 7.57 (1H,t); 7.42(1H,d); 7.33(2H,m); 7.11(1H,d); 5.42(2H,s); 4.67(2H,s); 2.41(3H,s).

C) Synthesis of 2-acetyloxybenzoic acid 6-(nitrooxymethyl)-2-methylpyridinyl ester To a solution of 2-acetyloxybenzoic acid 6-(chloromethyl)-2-methylpyridinyl ester (1.5 g, 4.7 mmoles) in acetonitrile (20 ml) kept under stirring, silver nitrate (1.3 g, 7.65 mmoles) is added. The solution is heated up to 80° C., maintaining it sheltered from light, under stirring for 30 hours. The formed silver chloride is filtered, the solvent is evaporated. The reaction raw product is purified by chromatography on silica gel eluting with n-hexane/ethyl acetate 7/3. 1.2 g of product as yellow oil are obtained.
$^1$H—NMR (200 MHz)(CDCl$_3$): 8.10(1H,d); 7.74(1H,t); 7.57 (1H,t); 7.42(1H,d); 7.33(2H,m); 7.11(1H,d); 5.60(2H,s); 5.42(2H,s); 2.41(3H,s).

D) Synthesis of 2-acetyloxybenzoic acid 6-(nitrooxymethyl-2-methpyridinyl ester hydrochloride To a solution of 2-acetyloxybenzoic acid 6-(nitrooxymethyl)-2-methylpyridinyl ester (1 g, 2.88 mmoles) in ethyl acetate (20 ml) cooled at 0° C., a solution of ethyl acetate/HCl 5M is added dropwise under stirring. It is left for 1 hour at 0° C., then the temperature is let reach room values. The formed precipitate is filtered and washed with ethyl ether. 900 mg of solid product are obtained.

Elementary Analysis

| | | | | | | | | |
|---|---|---|---|---|---|---|---|---|
| Calculated | C | 50.21% | H | 3.95% | N | 7.31% | Cl | 9.26% |
| Found | C | 50.23% | H | 3.97% | N | 7.29% | Cl | 9.20% |

$^1$H NMR (200 MHz) (CDCl$_3$): 8.10 (2H, m); 7.7 (1H, t); 7.56(2H, d); 7.48 (1H, t); 7.30(1H, d); 5.74 (2H, s); 5.43 (2H, s); 2.20 (3H, s).

Example 2

Synthesis of 2-acetyloxybenzoic acid 6-(nitrooxymethyl)-2-methylpyridinyl ester nitrate of Formula

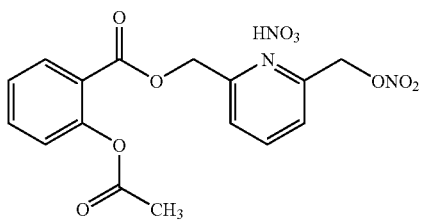

The 2-acetyloxybenzoic acid 6-(nitrooxymethyl)-2-methyl pyridinyl ester nitrate is obtained starting from the 2-acetyloxybenzoic acid 6-(nitrooxymethyl)-2-methylpyridinyl ester isolated at step C) of Example 1.

To a solution of 2-acetyloxybenzoic acid-6-(nitrooxymethyl)-2-methylpyridinyl ester (1 g, 2.88 mmoles) in acetonitrile (10 ml) cooled at 0° C., a solution of nitric acid 65% (0.2 ml) in acetonitrile (2 ml) is added dropwise under stirring. It is left for 2 hours at 0° C., then the temperature is let reach the room temperature. The formed precipitate is filtered and washed with ethyl ether. One gram of product as a solid is obtained.

Elementary Analysis

| Calculated | C | 46.95% | H | 3.69% | N | 10.26% |
|---|---|---|---|---|---|---|
| Found | C | 46.99% | H | 3.72% | N | 10.22% |

$^1$H NMR (200 MHz) (CDCl$_3$): 8.10 (1H, d); 7.9 (1H, t); 7.79(1H, t); 7.5 (3H, m); 7.30(1H, d); 5.73 (2H, s); 5.42 (2H, s); 2.20 (3H, s).

Example 3

Synthesis of 2-acetyloxybenzoic acid 5-(nitrooxymethyl)-2-methylpyridinyl ester hydrochloride of Formula

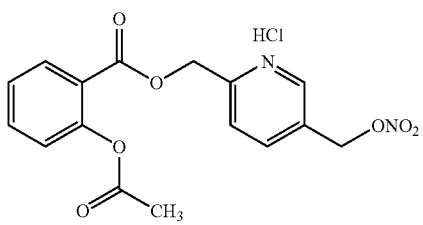

The 2-acetyloxybenzoic acid 5-(nitrooxymethyl)-2-methylpyridinyl ester hydrochloride is synthesized according to the process described in Example 1, starting from acetyl salicylic acid and 2,5-bis(chloromethyl)pyridine.

A) Synthesis of 2,5-bis(chloromethyl)-pyridine

The compound is synthesized according to the process described in Example 1 A) starting from 2,5-pyridin-dimethanol, sinthesized in its turn by reduction with NaBH$_4$ of di-ethyl-2,5-pyridin dicarboxylate in ethanol as described in patent JP 48029783.

Elementary Analysis

| Calculated | C | 50.21% | H | 3.95% | N | 7.32% | Cl | 9.26% |
|---|---|---|---|---|---|---|---|---|
| Found | C | 50.19% | H | 3.92% | N | 7.37% | Cl | 9.28% |

Example 4

Synthesis of 2-acetyloxybenzoic acid 3-(nitrooxymethyl)-2-methylpyridinyl ester hydrochloride of Formula

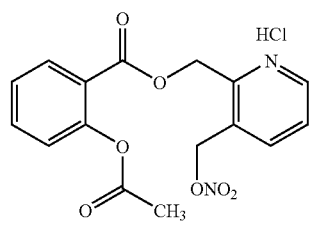

The 2-acetyloxybenzoic acid 3-(nitrooxymethyl)-2-methylpyridinyl ester hydrochloride is synthesized according to the process described in Example 1, starting from acetyl salicylic acid and 2,3-bis(chloromethyl)pyridine.

A) Synthesis of 2,3-bis(chloromethyl)-pyridine

The compound is synthesized according to the process described in Example 1 A) starting from 2,3-pyridin dimethanol, synthesized in its turn by reduction with LiAlH$_4$ of di-methyl-2,3-pyridindicarboxylate in ethanol as described in J. Chem. Soc., Perkin Trans. 1 (1972), (20), 2485-2490.

Elementary Analysis

| Calculated | C | 50.21% | H | 3.95% | N | 7.32% | Cl | 9.26% |
|---|---|---|---|---|---|---|---|---|
| Found | C | 50.25% | H | 3.93% | N | 7.30% | Cl | 9.29% |

Example 5

Synthesis of 3-nitrooxymethylphenyl ester of the 2-acetoxybenzoic acid

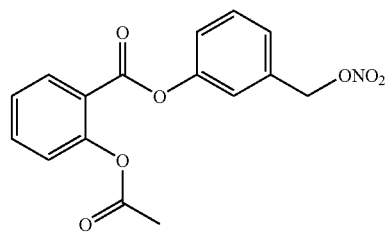

A) Preparation of 3-hydroxyethylohenyl ester of the 2-acetoxybenzoic acid 3-hydroxymethylphenol (10 g, 0.08 moles) is dissolved in toluene (50 ml) containing triethylamine (9.8 g, 0.1 moles).

To the so obtained solution, a solution of the acetylsalicylic acid chloride (16 g, 0.08 moles) in toluene (50 ml) is added under stirring at the temperature of 5-10° C. The mixture is maintained at a temperature within the above range, under stirring for 2 hours, then poured into water and then extracted with dichloromethane (2×100 ml). The organic phase is separated, washed in sequence with a solution of potassium carbonate at 25% w/v, with water, with a 3% hydrochloric acid solution and finally again with water, then anhydrified with sodium sulphate and the solvent evaporated under reduced pressure. The residue is crystallized from isopropanol. 3-hydroxymethyl phenyl ester of the 2-acetoxybenzoic acid (45.8 g, 0.16 moles, yield 80%) is obtained.

M.p.: 79-81° C.

$^1$H NMR(CDCl$_3$) δ (ppm): 2.29 (s, 3H); 4.71 (s, 2H); 7.07-8.2 (m, aromatics, 8H).

B) Nitration with fuming nitric acid in the presence of sulfuric acid of 3-hydroxymethylphenyl ester of the 2-acetoxybenzoic acid A solution of fuming nitric acid (3.92 g, 62.2 mmoles, 3 moles with respect to the moles of the hydroxyester under reaction) and sulphuric acid 96% (6.10 g, 62.2 mmoles, 3 moles with respect to the moles of the hydroxyester under reaction) in dichloromethane (25 ml) is cooled to 0° C. and added in one hour time under stirring and under nitrogen atmosphere, with a solution of 3-hydroxymethylphenyl ester of the 2-acetoxybenzoic acid (6 g, 20.7 mmoles) in 25 ml of dichloromethane. The mixture is then diluted with dichloromethane (50 ml) and poured into water and ice (100 g). The organic phase is separated, washed with water, anhydrified with sodium sulphate and the solvent evaporated under reduced pressure. The residue is crystallized from isopropanol obtaining the 3-nitrooxymethylphenyl ester of the 2-acetoxybenzoic acid (5.6 g, 17 mmoles, yield 82%).

M.p.: 61-62° C.

$^1$H NMR(CDCl$_3$) δ (ppm): 2.31 (s, 3H); 5.44 (s, 2H); 7.16-8.22 (m, aromatics, 8H).

Example 6

Synthesis of 2-(acetyloxy)benzoic acid 4-(nitrooxymethyl) phenyl ester

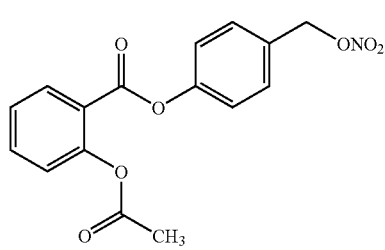

A) Synthesis of 2-(acetoxy)benzoic acid 3-(formyl)phenyl ester

To a mixture of 4-hydroxybenzaldeide (20.75 g, 0.17 moles) and triethylamine (0.205 g, 2.4 mmoles) in methylene chloride (300 ml) kept under stirring, under nitrogen inert atmosphere, cooling at a temperature in the range −5° C.-0° C., acetylsalicyloil chloride (41.25 g, 0.21 moles) is added in small aliquots in one hour. After 15 minutes water (250 ml) is added and the phases are separated. The aqueous phase is recovered and separately extracted with methylene chloride. The organic phases are mixed together, they are washed with a 5% carbonate solution (150 ml×2) and then with water (125 ml×2). The organic phase is anhydrified with sodium sulphate in the presence of decolorating carbon. It is filtered under vacuum and the solvent is evaporated under reduced pressure and at a bath temperature lower than 40° C., obtaining 48.2 g of 2-(acetyloxy)benzoic acid 4-(formyl)phenyl ester. The reaction raw product is used without further purification.

B) Synthesis of 2-(acetyloxy)benzoic acid 4-(hydroxymethyl) phenyl ester

A solution of 2-(acetyloxy)benzoic acid 4-(formyl)phenyl (48.2 g, 0.18 moles) ester in ethyl acetate (500 ml) is hydrogenated in the presence of 5% palladium on carbon (4 g) at room temperature, at hydrogen pressure of about 2.5 atm, under stirring. After 30 minutes the reactor is discharged, the catalyst is removed by filtration under nitrogen atmosphere.

The organic phase is washed with a 5% sodium bicarbonate solution and then with water. It is anhydrified with sodium sulphate and the solvent is evaporated at reduced pressure and the residue is used without further purification.

C) Synthesis of 2-(acetyloxy)benzoic acid 4-(chloromethyl) phenyl ester

To a mixture of 2-(acetyloxy)benzoic acid 4-(hydroxymethyl)phenyl (51.5 g, 0.18 moles) and SOCl$_2$ (153 ml) kept under stirring, dimethylformamide (140 ml) is added at room temperature and it is left under stirring for one hour. At the end the thionyl chloride is evaporated at reduced pressure at a bath temperature lower than 40° C. The thionyl chloride traces in the compound are removed by treating the solid with toluene (60×2), which is then removed by evaporation at reduced pressure at a bath temperature lower than 40° C. The raw product is purified by crystallization with isopropyl ether to give 2-(acetyloxy)benzoic acid 4-(chloromethyl)phenyl ester (32.9 g, 0.10 moles). Yield 60%.

$^1$H NMR: 8.25 (1H, d); 7.68 (1H, t); 7.43 (3H, m); 7.20 (3H, m); 4.60 (2H, s); 2.34 (3H, s).

D) Synthesis of 2-(acetyloxy)benzoic acid 4-(nitrooxymethyl) phenyl ester

To a solution of 2-(acetyloxy)benzoic acid 4-(chloromethyl)phenyl ester (32.9 g, 0.10 moles) in acetonitrile silver nitrate (22.2 g, 0.12 moles) is added under stirring, sheltered from light. The solution is heated at 70° C. for 4 hours and then cooled to room temperature. The precipitate is filtered and the solvent evaporated at reduced pressure.

The residue is purified by chromatography on silica gel eluting with hexane/ethyl acetate (7:3 v/v) to give 2-(acetyloxy)benzoic acid 4-(nitrooxymethyl)phenyl ester (16.6 g, 0.05 moles). M.p. 86-88° C. Yield 50%.

$^1$H NMR (CDCl$_3$): 8.21 (1H, dd); 7.66 (1H,dt); 7.42 (3H,m); 7.20 (3H,m); 5.40 (2H, s), 2.25 (3H,s).

Example 7

Synthesis of trans-3-[4-[2-(acetyloxy)benzoyloxy]-3-methoxyphenyl]-2-propenoic acid 4-(nitrooxy) butyl ester

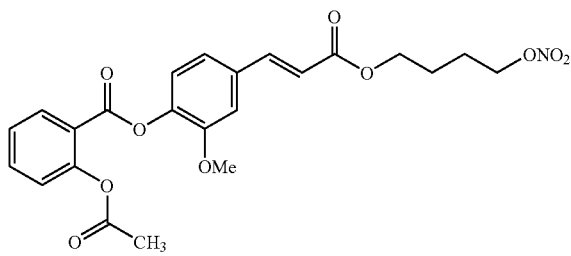

A) Synthesis of trans-3-[4-hydroxy-3-methoxyphenyl]-2-propenoic acid 4-bromo butyl ester To a solution of ferulic acid (10 g, 51.5 mmoles) in THF (400 ml) and cooled in a water bath, triphenylphosphine (27.01 g, 103 mmoles) and carbon tetrabromide (34.1 g, 103 mmoles) are in the order added. The mixture is kept under stirring for 5 hours at room temperature. When the reaction is ended, triphenylphosphinoxide is filtered and the solvent is evaporated at reduced pressure. The residue is purified by chromatography on silica gel eluting with hexane/ethyl acetate (7:3 v/v). 7.75 g of trans-3-[4-hydroxy-3-methoxyphenyl]-2-propenoic acid 4-bromobutyl ester as a white solid are obtained. M.p. 86-89° C. Yield 46%.

B) Synthesis of trans-3-[4-[2-(acetyloxy)benzoyloxy]-3-methoxyphenyl]-2-propenoic acid 4-bromo butyl ester To a solution of trans 3-[4-hydroxy-3-methoxyphenyl]-2-propenoic acid 4-bromo butyl ester (2 g, 6.1 mmoles) in $CHCl_3$ (20 ml) an acetylsalicylic acid mixture (1.1 g, 6.1 mmoles) in DMF (2 ml) is added and it is cooled to 0° C., then DCC (1.50 g, 7.2 mmoles) and DMAP (74 mg, 6×10$^{-3}$ mmoles) are added. It is left at the same temperature for 30 minutes and at room temperature for 16 hours. The precipitate is filtered and the solvent is evaporated at reduced pressure. The residue is dissolved in ethyl acetate (100 ml×2 times) and washed with water and NaCl. The organic phase is anhydrified and the solvent is evaporated at reduce pressure.

The residue is purified by chromatography on silica gel eluting with hexane/ethyl acetate (8:2 v/v) to give the trans-3-[4-[2-(acetyloxy)benzoyloxy]-3-methoxyphenyl]-2-propenoic acid 4-bromo butyl ester (1.1 g, Yield 37%).

$^1$H NMR CDCl$_3$: 8.25 (1H, d); 7.65 (2H, m); 7.40 (1H, t); 7.20 (4H, m); 6.39 (1H, d); 4.25 (2H, t); 3.85 (3H, s); 3.47 (2H, t); 2.29 (3H, s); 2.01 (2H, m); 1.89 (2H, m).

Example 8

Synthesis of trans-3-[4-(4'-nitrooxybutyryloxy)-3-methoxyphenyl]-2-propenoic acid 4-(acetylamino) phenyl ester

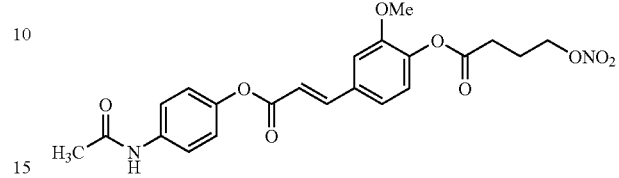

A) Synthesis of trans-3-[4-acetyloxy-3methoxyphenyl]-2-propenoic acid

To a solution of ferulic acid (5 g, 25.75 mmoles) in pyridine (75 ml) cooled to 0° C. and sheltered from light, acetic anhydride (13.14 g, 128.7 mmoles) is added in small aliquots. When the addition is ended the temperature is let reach the room value maintaining the solution under magnetic stirring for 24 hours. HCl 18.5% (160 ml) is added up to pH 2, one extracts with ethyl acetate and the organic phase is anhydrified and the solvent is evaporated at a reduced pressure. 5.15 g of trans-3-[4-acetyloxy-3-methoxyphenyl]-2-propenoic acid are obtained as a white solid. M.p. 199-205° C. Yield 85%.

B) Synthesis of trans-3-[4-acetyloxy-3-methoxyphenyl]-2-propenoyl chloride

To a suspension of trans-3-[4-acetyloxy-3-methoxyphenyl]-2-propenoic acid (4 g, 16.93 mmoles) in toluene (70 ml) and dimethylformamide (10 ml) cooled in an ice bath, oxalyl chloride (4.30 g, 33.87 mmoles) is dropped. The mixture is maintained under stirring at 0° C. for 1 hour then the temperature is let reach the room value and it is left for 2 hours. The solvent is removed at reduced pressure and the raw product is used without further purification.

C) Synthesis of trans-3-[4-acetyloxy-3-methoxyphenyl]-2-propenoic acid 4-(acetylamino)phenyl ester To a solution of paracetamol (2.56 g, 16.92 mmoles) in pyridine (20 ml) cooled in an ice bath trans-3-[4-acetyloxy-3-methoxyphenyl]-2-propenoyl chloride (4.31 g, 16.92 mmoles) dissolved in acetone (45 ml) is dropped. The mixture is maintained under stirring in ice for 3 hours then it is poured into water (300 ml) and the precipitate is filtered and triturated with hexane to give trans-3-[4-acetyloxy-3-methoxyphenyl]-2-propenoic acid 4-(acetylamino)phenyl ester (4.38 g) as an orange solid. M.p. 246-250° C. Yield 70%.

D) Synthesis of trans-3-[4-hydroxy-3-methoxyphenyl]-2-propenoic acid 4-(acetylamino)phenyl ester To a solution of trans-3-[4-acetyloxy-3-methoxyphenyl]-2-propenoic acid 4-(acetylamino)phenyl ester (4.2 g, 11.37 mmoles) in methanol (650 ml) and tetrahydrofuran (850 ml), potassium carbonate (9.11 g, 65.95 mmoles) dissolved in water (50 ml) is added and it is left under stirring at room temperature for 2 hours. The precipitate is filtered and the solution is brought to pH 6 with HCl 5% (15 ml). One extracts with ethyl acetate and the organic phase is anhydrified and removed from the solvent at reduced pressure. The raw product is purified by chromatography on silica gel eluting with chloroform/methanol (9/0.5 v/v). Trans-3-[4-hydroxy-3-methoxyphenyl]-2-propenoic acid 4-(acetylamino)phenyl ester (2.1 g) is obtained as a white solid. M.p. 185-195° C. Yield 56%.

$^1$H NMR (CDCl$_3$): 10 (1H, s); 9.8 (1H,s); 7.8 (1H, d); 7.7 (2H, d); 7.3 (2H,d); 7.1 (2H, d); 6.9 (1H, d); 6.7 (1H, d); 3.8 (3H, s); 2 (3H, s).

E) Synthesis of trans-3-[4-(4'-bromobutyryloxy)-3-methoxyphenyl]-2-propenoic acid 4-(acetylamino) phenyl ester To a solution of trans-3-[4-hydroxy-3-methoxyphenyl]-2-propenoic acid 4-(acetylamino)phenyl ester (1.6 g, 4.8 mmoles) in pyridine (12 ml) cooled in ice bath, 4-bromobutyryl chloride (1.3 g, 7.2 mmoles) dissolved in acetone (15 ml) is dropped and it is maintained under stirring for 7 hours. It is poured into water and ice, the precipitate is filtered and treated with hexane. Trans-3-[4-(4'bromobutyryloxy)-3-methoxyphenyl]-2-propenoic acid 4-(acetylamino)phenyl ester (1.8 g) is obtained. Yield 67%.

F) Synthesis of trans-3-[4-(4'-nitrooxybutyryloxy)-3-methoxyphenyl]-2-propenoic acid 4-(acetylamino) phenyl ester To a solution of trans-3-[4-(4'bromobutyryloxy)-3-methoxyphenyl]-2-propenoic acid 4-(acetylamino)phenyl ester (1.8 g, 3.78 mmoles) in acetonitrile (100 ml), silver nitrate (1.28 g, 7.56 mmoles) is added sheltered from light. It is left at 80° C. for 13 hours then the precipitate is filtered. The raw product is purified by chromatography on silica gel eluting with hexane/ethyl acetate (3/7 v/v). Trans-3-[4-(4'nitrooxybutyryloxy)-3-methoxyphenyl]-2-propenoic acid 4-(acetylamino)phenyl ester is obtained.

$^1$H NMR (CDCl$_3$): 7.8 (1H, d); 7.5 (3H,m); 7.1 (5H, m); 6.5 (1H, d); 4.6 (2H, t); 3.8 (3H, s); 2.7 (2H, t); 2.17 (5H,m).

Example 9

Synthesis of 4-nitrooxybutanoic acid 4'-acetylamino phenyl ester

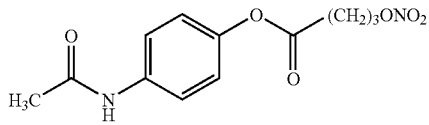

A) Preparation of 4-bromobutanoic acid 4'-acetylamino phenyl ester

To a solution of 4-bromobutyric acid (4.6 g, 27.6 mmoles) in chloroform (45 ml) and N,N-dimethylformamide (20 ml), paracetamol (4.17 g, 27.6 mmoles), N,N'-dicyclohexyl carbodiimide (8.42 g, 40.8 mmoles) and 4-dimethyl aminopyridine (0.15 g, 1.25 mmoles) are added. The reaction mixture is kept under stirring at room temperature for 72 hours, filtered and evaporated under vacuum. The reaction raw product is treated with ethyl acetate and washed with brine and then with water. The organic phase is anhydrified with sodium sulphate and then evaporated under vacuum.

The residue is purified by chromatography on silica gel eluting with n-hexane/ethyl acetate 4/6 (v/v ratio). 5.33 g of the product as a white solid ar obtained.

M.p.=108-110° C.

B) Preparation of 4-nitrooxybutanoic acid 4'-acetylamino phenyl ester

To a solution of 4-bromobutanoic acid 4'-acetylamino phenyl ester (5.33 g, 17.8 mmoles) in acetonitrile (80 ml) silver nitrate (4.56 g, 26.9 mmoles) is added. The reaction mixture is heated for 16 hours in absence of light at 80° C., then cooled to room temperature, filtered for removing the silver salts, and evaporated at reduced pressure. The residue is purified by chromatography on silica gel, eluting with n-hexane/ethyl acetate 4/6. 4.1 g of the product as a white solid are obtained.

M.p.=80-83° C.

| Elementary analysis: | C | H | N |
|---|---|---|---|
| calc. | 51.07% | 4.99% | 9.92% |
| found | 51.06% | 5.00% | 9.90% |

$^1$H NMR (CDCl$_3$): 7.55 (1H, s); 7.49 (2H,d); 7.02 (2H,d); 4.58 (2H, t); 2.71 (2H,t); 2.19 (2H, m); 2.14 (3H,s).

Example 10

Syntheis of 4-(nitrooxymethyl)-benzoic acid 4-acetylamino phenyl ester

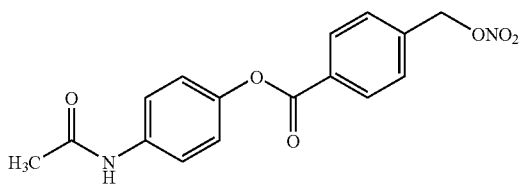

A) Preparation of 4-(chloromethyl)-benzoic acid 4-acetylamino phenyl ester

To a solution of paracetamol (2 g, 13.23 mmoles) in tetrahydrofuran (80 ml), triethylamine (1.34 g, 13.23 mmoles) and 4-(chloromethyl)-benzoylchloride (2.5 g, 13.23 mmoles) are added. The reaction mixture is kept under stirring at room temperature for 24 hours, then the solvent is evaporated at reduced pressure and the reaction raw product is purified by chromatography on silica gel, eluting with methylene chloride/methanol 20/0.5 (v/v ratio) to give 2.6 g of 4-(chloromethyl)-benzoic acid 4-acetylamino phenyl ester. (Yield 65%)

$^1$H NMR (CDCl$_3$): 8.1 (2H, d); 7.69 (2H,d); 7.45 (2H, d); 7.02 (2H, d); 4.9 (2H, s); 2.14 (3H, s).

B) Preparation of 4-(nitrooxymethyl)-benzoic acid 4-acetylamino phenyl ester

To a solution of 4-(chloromethyl)-benzoic acid 4-acetylamino phenyl ester (2 g, 6.6 mmoles) in acetonitrile (80 ml) silver nitrate (2.24 g, 13.18 mmoles) is added. The reaction mixture is heated for 20 hours in absence of light at 60° C., then cooled to room temperature, filtered for removing the silver salts, and evaporated at reduced pressure. The residue is purified by chromatography on silica gel, eluting with n-hexane/ethyl acetate 3/7 (v/v ratio). 1.13 g of 4-(nitrooxymethyl)-benzoic acid 4-acetylamino phenyl ester are obtained. (Yield 52%)

$^1$H NMR (CDCl$_3$): 8.1 (2H, d); 7.69 (2H,d); 7.45 (2H, d); 7.02 (2H, d); 5.74 (2H, s); 2.14 (3H, s).

Example 11

Preparation of 3-(nitrooxymethyl)-benzoic acid 4-acetylamino phenyl ester

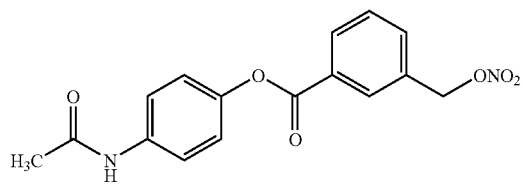

A) Preparation of 3-(chloromethyl)-benzoic acid 4-acetylamino phenyl ester

To a solution of paracetamol (2 g, 13.23 mmoles) in tetrahydrofuran (80 ml), triethylamine (1.34 g, 13.23 mmoles) and 4-(chloromethyl)-benzoylchloride (2.5 g, 13.23 mmoles) are added. The reaction mixture is kept under stirring at room temperature for 24 hours, then the solvent is evaporated at reduced pressure and the reaction raw product is purified by chromatography on silica gel, eluting with methylene chloride/methanol 20/0.5 (v/v ratio) to give 2.9 g of 3-(chloromethyl)-benzoic acid 4-acetylamino phenyl ester. (Yield 73%)

$^1$H NMR (CDCl$_3$): 8.1 (1H, s); 8.02 (1H,d); 7.77 (1H, d); 7.65 (1H, m); 7.45 (2H, d); 7.02 (2H,d); 4.9 (2H, s); 2.14 (3H, s).

B) Preparation of 3-(nitrooxymethyl)-benzoic acid 4-acetylamino phenyl ester

To a solution of 3-(chloromethyl)-benzoic acid 4-acetylamino phenyl ester (2.5 g, 8.2 mmoles) in acetonitrile (80 ml) silver nitrate (2.8 g, 16.4 mmoles) is added. The reaction mixture is heated for 20 hours in absence of light at 60° C., then cooled to room temperature, filtered for removing the silver salts, and evaporated at reduced pressure. The residue is purified by chromatography on silica gel, eluting with n-hexane/ethyl acetate 3/7 (v/v ratio). 1.5 g of 3-(nitrooxymethyl)-benzoic acid 4-acetylamino phenyl ester are obtained. (Yield 55%)

$^1$H NMR (CDCl$_3$): 8.1 (1H, s); 8.02 (1H,d); 7.77 (1H, d); 7.65 (1H, m); 7.45 (2H, d); 7.02 (2H,d); 5.74 (2H, s); 2.14 (3H, s).

Example 12

Synthesis of 2-(nitrooxymethyl)-benzoic acid 4-acetylamino phenyl ester

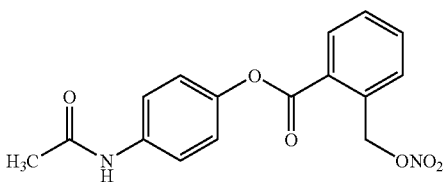

A) Preparation of 2-(chloromethyl)-benzoylchloride

To thionyl chloride (35 ml) cooled at 0° C. with ice bath, the 2-hydroxymethylbenzoic acid (4 g, 26.3 mmoles) is added. The temperature is let reach the room value and the mixture is left under stirring for 2 hours, then it is evaporated at reduced pressure and treated 3 times with chloroform for completely removing the thionyl chloride. The reaction raw product is used without further purification.

B) Preparation of 2-(chloromethyl)-benzoic acid 4-acetyl amino phenyl ester

To a solution of paracetamol (2 g, 13.23 mmoles) in tetrahydrofuran (80 ml), triethylamine (1.34 g, 13.23 mmoles) and 2-(chloromethyl)-benzoylchloride (2.5 g, 13.23 mmoles) are added. The reaction mixture is kept under stirring at room temperature for 24 hours, then the solvent is evaporated at reduced pressure and the reaction raw product is purified by chromatography on silica gel, eluting with methylene chloride/methanol 20/0.5 (v/v ratio) to give 1.9 g of 2-(chloromethyl)-benzoic acid 4-acetylamino phenyl ester. (Yield 47%)

$^1$H NMR (CDCl$_3$): 8.22 (1H, d); 7.41 (5H, m); 7.02 (2H, d); 4.9 (2H, s); 2.14 (3H, s).

C) Preparation of 2-(nitrooxymethyl)-benzoic acid 4-acetylamino phenyl ester

To a solution of 2-(chloromethyl)-benzoic acid 4-acetylamino phenyl ester (1.5 g, 4.9 mmoles) in acetonitrile (80 ml) silver nitrate (1.68 g, 9.8 mmoles) is added. The reaction mixture is heated for 20 hours in absence of light at 60° C., then cooled to room temperature, filtered for removing the silver salts, and evaporated at reduced pressure. The residue is purified by chromatography on silica gel, eluting with n-hexane/ethyl acetate 3/7 (v/v ratio). 0.77 g of 2-(nitrooxymethyl)-benzoic acid 4-acetylamino phenyl ester are obtained. (Yield 48%)

$^1$H NMR (CDCl$_3$): 8.22 (1H, d); 7.41 (5H, m); 7.02 (2H, d); 5.40 (2H, s); 2.14 (3H, s).

Example 13

Synthesis of 2-acetylamino-3-(4-nitrooxybutyryl)-3-mercaptopropionic acid 4-acetylamino phenyl ester

A) Preparation of 2-acetylamino-3-(4-bromobutyryl)-3-mercantopropionic acid

To a solution of 4-bromobutyric acid (3 g, 17.9 mmoles) in 35 ml of chloroform, carbonyl-diimidazol (2.9 g, 17.9 mmoles) is added and it is left under stirring at room temperature for one hour. Then N-acetylcisteine (2.9 g, 17.9 mmoles), sodium ethylate (40 mg, 0.58 mmoles) and dimethylformamide (5 ml) are added and the mixture is left under stirring at room temperaturte for 15 hours. Diluted HCl is added and the organic phase is separated. The aqueous phase brought to pH 3-3.5 is extracted with ethyl acetate. The organic phases mixed together are anhydrified with sodium sulphate and evaporated at reduced pressure. The reaction raw product is purified by chromatography on silica gel, eluting with chloroform/ethyl acetate 3/7 (v/v ratio). 2.06 g of 2-acetylamino-3-(4-bromobutyryl)-3-mercapto-propionic acid are obtained. (Yield 37%)
$^1$H NMR (CDCl$_3$): 10.0 (1H, s); 6.89 (1H, d); 4.78 (1H, m); 3.40 (4H, m); 2.77 (2H, t); 2.18 (2H, m); 2.04 (3H, s).

B) Preparation of 2-acetylamino-3-(4-bromobutyryl)-3-mercaptopropionic acid 4-acetylamino phenyl ester To a solution of 2-acetylamino-3-(4-bromobutyryl)-3-mercaptopropionic acid in chloroform (20 ml) and dimethylformamide (20 ml), cooled at 0° C. with ice bath, paracetamol (1 g, 7.2 mmoles), dicyclohexylcarbodiimide (1.17 g, 5.6 mmoles) and N,N-dimethyl aminopyridine (90 mg) are added. The temperature is let reach the room value and the mixture is left under stirring for 24 hours. The precipitate is filtered and the organic phase is washed with water. The organic phase is anhydrified with sodium sulphate and the solvent is evaporated at reduced pressure. The raw product has been purified by chromatography on silica gel eluting with methylene chloride/methanol 20/0.5 (v/v ratio). 0.6 g of 2-acetylamino-3-(4-bromobutyryl)-3-mercaptopropionic acid 4-acetylamino phenyl ester are obtained. (Yield 32%)
$^1$H NMR (CDCl$_3$): 7.45 (2H, d); 7.00(2H, m); 4.80 (1H, m); 3.52 (2H, t); 3.32 (2H,d); 2.7 (2H,t); 2.1 (2H, m); 2.00 (3H, s).

C) Preparation of 2-acetylamino-3-(4-nitrooxy butyryl)-3-mercaptopropionic acid 4-acetylamino phenyl ester To a solution of 2-acetylamino-(4-bromobutyryl)-3-mercaptopropionic acid 4-acetylamino phenyl ester (0.5 g, 1.26 mmoles) in acetonitrile (40 ml) silver nitrate (0.43 g, 2.52 mmoles) is added. The reaction mixture is heated for 20 hours in absence of light at 80° C., then cooled to room temperature, filtered for removing the silver salts, and evaporated at reduced pressure. The residue is purified by chromatography on silica gel, eluting with n-hexane/ethyl acetate 3/7 (v/v ratio). 0.31 g of 2-acetylamino-3-(4-nitrooxybutyryl)-3-mercaptopropionic acid 4-acetylamino phenyl ester are obtained. (Yield 63%)
$^1$H NMR (CDCl$_3$): 7.45 (2H, d); 7.00(2H, m); 4.80 (1H, m); 4.57 (2H, t); 3.32 (2H,d); 2.7 (2H,t); 2.1 (2H, m); 2.00 (3H, s).

Example 14

Synthesis of 3-[(2-nitrooxy)ethyloxy]propanoic acid 4-acetylamino phenyl ester

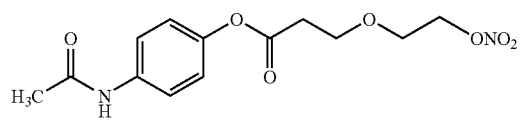

A) Preparation of 3-[(2-hydroxy)ethyloxy]propanoic acid 4-acetylamino phenyl ester To a solution of paracetamol (5 g, 33.6 mmoles) in chloroform (80 ml) and dimethylformamide (80 ml), cooled at 0° C. with ice bath, 3-[(2-hydroxy)ethyloxy]propanoic acid (3 g, 22.38 mmoles), dicyclohexylcarbodiimide (6.9 g, 33.6 mmoles) and dimethylaminopyridine (0.2 g, 1.68 mmoles) are added. The temperature is let reach the room value and the mixture is left under stirring for 24 hours. The precipitate is filtered and the organic phase is washed with water and extracted with chloroform. The organic phase is anhydrified with sodium sulphate and the solvent evaporated at reduced pressure. The raw product is purified by chromatography on silica gel eluting with methylene chloride/methanol 20/0.5 (v/v ratio). 1.3 g of 3-[(2-hydroxy)ethyloxy]propanoic acid 4-acetylamino phenyl ester are obtained. (Yield 33%)
$^1$H NMR (CDCl$_3$): 7.45 (2H, d); 7.02(2H, d); 4.40 (2H, t); 3.75 (6H,m); 2.14 (3H, S).

B) Preparation of 3-[(2-iodo)ethyloxy]propanoic acid 4-acetylamino phenyl ester To a solution of 3-[(2-hydroxy)ethyloxy]propanoic acid 4-acetylamino phenyl ester (1.5 g, 5.6 mmoles), imidazol (0.57 g, 8.4 mmoles) and triphenylphosphine (1.9 g, 7.28 mmoles) in ether (15 ml) and acetonitrile (10 ml) cooled at 0° C. with ice bath, iodine (1.99 g, 7.84 mmoles) is added and it is left under stirring at 0° C. for 2 hours. Then the temperature is let reach the room value, hexane is added, the precipitate is filtered and the solvent is evaporated at reduced pressure. The raw product is purified by chromato-graphty on silica gel eluting with hexane/ethyl acetate 3/7 (v/v ratio). 1 g of 3-[(2-iodo)ethyloxy]propanoic acid 4-acetylamino phenyl ester is obtained.

(Yield 48%)
$^1$H NMR (CDCl$_3$): 7.45 (2H, d); 7.02(2H, d); 4.40 (2H, t); 3.75 (4H,t); 3.54 (2H, t); 2.14 (3H, s).

C) Preparation of 3-[(2-nitrooxy)ethyloxy]propanoic acid 4-acetylamino phenyl ester To a solution of 3-[(2-iodo)ethyloxy]propanoic acid 4-acetylamino phenyl ester (1 g, 2.64 mmoles) in acetonitrile (40 ml) silver nitrate (0.9 g, 5.28 mmoles) is added. The reaction mixture is heated for 5 hours in absence of light at 60° C., then cooled to room temperture, filtered for removing the silver salts, and evaporated at reduced pressure. The residue is purified by chromatography on silica gel, eluting with n-hexane/ethyl acetate 3/7 (v/v ratio). 0.46 g of 3-[(2-nitrooxy)ethyloxy]propanoic acid 4-acetylamino phenyl ester are obtained. (Yield 56%)

$^1$H NMR (CDCl$_3$): 7.45 (2H, d); 7.02(2H, d); 4.58 (2H, t); 4.40 (2H, t); 3.75 (4H, t); 2.14 (3H, s).

Example 15

Synthesis of 2-hydroxybenzoic acid 3-(nitrooxymethyl) phenyl ester

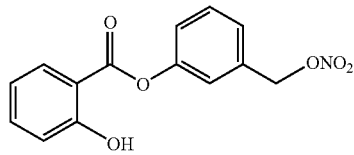

To a solution of 2-(acetyloxy)benzoic acid 3-(nitroxymethyl)phenylester (2 g, 6.04 mmoles), obtained as described in Example 5, in tetrahydrofuran (10 ml), methanol (5 ml) and water (4 ml), imidazol (0.04 g, 0.6 mmoles) is added. The mixture is left under stirring at room temperature for 20 days, then the solvent is evaporated at reduced pressure, the residue is treated with ethyl acetate and washed with water.

The organic phase is anhydrified with sodium sulphate and the solvent is evaporated at reduced pressure. The reaction raw product is purified by chromatography on silica gel using as eluent hexane/ethyl acete (9/1 v/v) to give 2-hydroxybenzoic acid 3-(nitrooxymethyl)phenylester (0.8 g). Yield 46%.

$^1$H NMR (CDCl$_3$): 10.46 (1H, s); 8.13 (1H, dd); 7.56 (2H, m); 7.34 (3H, m); 7.05(2H, m); 5.51(2H, s).

Example 16

Synthesis of trans-3-[4-[α-methyl-[4-(-2-methylpropyl)benzene]acetyloxy]-3-methoxyphenyl]-2-propenoyl 4-(nitrooxy) butyl ester Having Formula

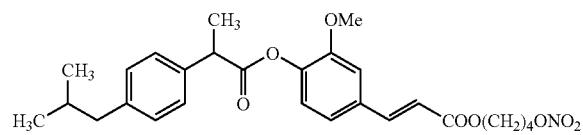

A) Synthesis of trans-3-[4-[α-methyl-[4-(-2-methylpropyl) benzene]acetyloxy]-3-methoxyphenyl]-2-propenoic acid To a solution of α-methyl-[4-(2-methylpropyl)benzene] acetic acid (5.03 g, 24.4 mmoles) in tetrahydrofuran (100 ml) and N,N-dimethylformaide (5 ml), 1,1-carbonyldiimidazol (4.25 g, 24.8 mmoles) is added. After 1 hour the obtained solution is treated with ferulic acid (4.90 g, 25 mmoles), sodium ethylate (89 mg) is added and it is left at room temperature under stirring for 12 hours. The reaction mixture is washed with HCl 5%, then with water and at last with brine. The organic phase is anhydrified with sodium sulphate and evaporated at reduced pressure.

The obtained residue is purified by chromatography on silica gel, eluting with ethyl acetate/n-hexane 7/3. 5.1 g of trans-3-[4-[α-methyl-[4-(-2-methylpropyl)benzene]acetyl]-3-methoxyphenyl]-2-propenoic acid are obtained as a withe solid having m.p. 131-137° C.

$^1$H-NMR (CDCl$_3$): 7.72 (1H, d), 7.32 (2H, dd), 7.26 (1H, m), 7.16-7.07 (4H, m), 6.98 (1H, d), 6.37 (1H, d), 3.99 (1H, q), 3.73 (3H, s), 2.47 (2H, d), 1.88 (1H, m), 1.63 (3H, d), 0.92 (6H, d).

B) Synthesis of trans-3-[4-[α-methyl-[4-(-2-methylpropyl) benzene]acetyloxy]-3-methoxyphenyl]-2-propenoyl 4-bromobutyl ester To a solution of trans-3-[4-[α-methyl-[4-(2-methylpropyl) benzene]acetyloxy]-3-methoxyphenyl]-2-propenoic acid (5.33 g, 14 mmoles) in N,N-dimethylformamide (130 ml), sodium ethylate (1.2 g, 16 mmoles) is added under stirring. After 1 hour to the obtained mixture 1,4-dibromobutane (10 g, 46 mmoles) is added and the mixture is let react at room temperature for 12 hours. The reaction mixture is washed with 5% HCl, then with water and at last with brine, the organic phase is anhydrified with sodium sulphate and evaporated at reduced pressure. The obtained residue is purified by chromatography on silica gel eluting with n-hexane/ethyl acetate 8/2. 4.46 g of trans-3-[4-hydroxy-[α-methyl-[4-(-2-methylpropyl)benzene]acetyl]-3-methoxyphenyl]-2-propenoyl 4-bromobutyl ester are obtained.

C) Synthesis of trans-3-[4-[α-methyl-[4-(-2-methylpropyl) benzene]acetyloxy]-3-methoxyphenyl]-2-propenoyl 4-(nitrooxy) butyl ester To a solution of trans-3-[4-[α-methyl-[4-(-2-methylpropyl)benzene]acetyloxy]-3-methoxyphenyl]-2-propenoyl 4-bromobutyl ester (4 g, 7.72 mmoles) in acetonitrile (70 ml) silver nitrate (2.58 g, 15 mmoles) is added. The reaction mixture is heated under reflux for 2 hours sheltered from light. At the end the formed salt is removed by filtration and the solution is evaporated at reduced pressure. The recovered residue is purified by chromatography on silica gel, eluting with n-hexane/ethyl acetate 8/2. 2.4 g of trans-3-[4-[α-methyl-[4-(-2-methylpropyl)benzene]acetyloxy]-3-methoxyphenyl]-2-propenoyl 4-(nitrooxy) butyl ester are obtained as oil.

$^1$H-NMR (CDCl$_3$): 7.62 (1H, d), 7.32 (2H, d), 7.15 (2H, d), 7.16-7.05 (2H, m), 6.96 (1H, d), 6.35 (1H, d), 4.51 (2H, t), 4.24 (2H, t), 3.99 (1H, q), 3.74 (3H, s), 2.48 (2H, d), 1.89-1.83 (5H, m), 1.62 (3H, d), 0.92(6H, d).

Elementary Analysis:

| | | | | | | | |
|---|---|---|---|---|---|---|---|
| Calculated | C: | 64.91% | H: | 6.66% | N: | 2.82% |
| Found | C: | 64.83% | H: | 6.52% | N: | 2.69% |

Example 17

Syntheis of trans-3-[4-[2-fluoro-α-methyl-(1,1'-biphenyl)-4-acetyloxy]-3-methoxyphenyl]-2-propenoyl 4-(nitrooxy) butyl ester having formula

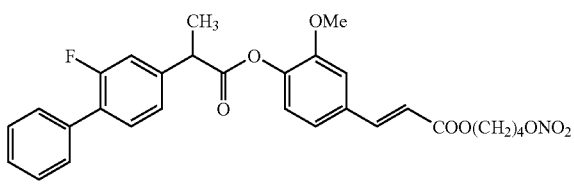

The compound is synthesized according to the process described in Example 16. The process total yield is 32%. The susbstance appears as an amorphous solid.

$^1$H—NMR (CDCl$_3$): 7.40-7.25 (9H, m), 7.07-7.01 (2H, d), 6.98 (1H, m), 6.38 (1H, d), 4.44 (2H, t), 4.46 (2H, t), 4.21 (2H, t), 4.04 (1H, q), 3.73 (3H, s), 1.72 (4H, m), 1.65 (3H, d).

Elementary Analysis:

| Calculated | C: 64.79% | H: 5.25% | N: 2.62% | F: 3.53% |
|---|---|---|---|---|
| Found | C: 64.85% | H: 5.31% | N: 2.74% | F: 3.48% |

Example 18

Syntheis of (Z)-5-fluoro-2-methyl-1-[[4-(methylsulphinyl phenyl]methylene]-1H-indene-3-acetic acid (4-nitrooxy)butyl ester

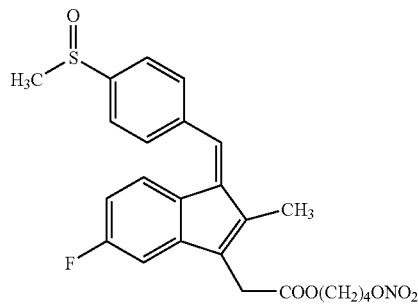

A) Synthesis of (Z)-5-fluoro-2-methyl-1-[[4-(methylsulphinyl) phenyl]methylene]-1H-indene-3-acetic acid 4-bromobutyl ester To a solution of Sulindac (5.17 g, 14.5 mmoles) in dimethylformamide (50 ml) EtONa (1.18 g, 16.4 mmoles) is added. The reaction mixture is kept under stirring for one hour, then 1,4-dibromobutane dissolved in dimethylformamide, (20 ml) is added.

The reaction mixture is kept under stirring at room temperature for 8 hours, ethyl acetate is added and the mixture is washed with water. The organic phase is anhydrified with sodium sulphate and the solvent is evaporated at reduced pressure.

The reaction raw product is purified by chromatography on silica gel eluting with a mixture of hexane/ethyl acetate (3/7 v/v). Cis-5-fluoro-2-methyl-1-[[4-(methylsulphinyl) phenyl]methylene]-1H-indene-3-acetic acid 4-bromobutyl ester (3.8 g) is obtained as a yellow solid. Yield 55%.

B) Synthesis of (Z)-5-fluoro-2-methyl-1-[[4-(methylsulphinyl) phenyl]methylene]1H-indene-3-acetic acid (4-nitrooxy)butyl ester To a solution of cis-5-fluoro-2-methyl-1-[[4-(methyl sulphinyl)phenyl]methylene]-1H-indene-3-acetic acid 4-bromo-butyl ester (3.8 g, 7.7 mmoles) in acetonitrile (50 ml) AgNO$_3$ (3.9 g, 22.3 mmoles) is added sheltered from light. The mixture is heated at 80° C. for 48 hours, then the precipitate is filtered and the solvent is evaporated. The reaction raw product is purified by chromatography on silica gel eluting with a mixture of hexane/ethyl acetate (1/9 v/v). (Z)-5-fluoro-2-methyl-1-[[4-(methylsulphinyl) phenyl]methylene]-1H-indene-3-acetic acid (4-nitrooxy)butyl ester (2.6 g) is obtained as a yellow solid. Yield 68%.

$^1$H NMR (CDCl$_3$): 7.78-7.62 (4H, m); 7.17 (2H, m); 6.88 (1H, dd); 6.60-6.50 (1H, m); 4.39 (2H, t); 4.16 (2H, t); 3.57 (2H, s); 2.79 (3H, s); 2.20 (3H, s); 1.79-1.61 (4H, m).

Example 19

Synthesis of (Z)-5-fluoro-2-methyl-1-[[4-(methylsulphinyl) phenyl]methylene]-1H-indene-3-acetic acid 6(nitrooxymethyl)-2-methyl pyiridinyl ester

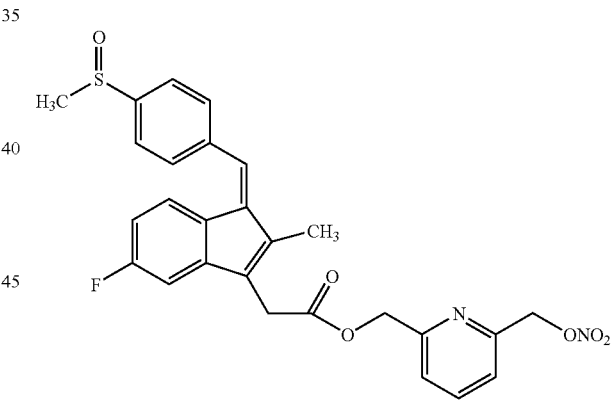

The (Z)-5-fluoro-2-methyl-1-[[4-(methylsulphinyl)phenyl]methylene]-1H-indene-3-acetic acid 6(nitrooxymethyl)-2-methyl pyridinyl ester is synthesized according to the process described in Example 1, starting from (Z)-5-fluoro-2-methyl-1-[[4-(methylsulphinyl)phenyl]methylene]-1H-indene-3-acetic acid and 2,6-bis (chloromethyl)pyridine. Total yield of the process 20%.

Elementary Analysis:

| Calculated | C 57.09% | N 5.12% | F 3.47% | Cl 6.48% | S 5.86% |
|---|---|---|---|---|---|
| Found | C 57.19% | N 4.51% | F 3.43% | Cl 6.51% | S 5.84% |

Example 20

Synthesis of 2-acetyloxybenzoic acid 2-(nitrooxymethyl)phenyl ester

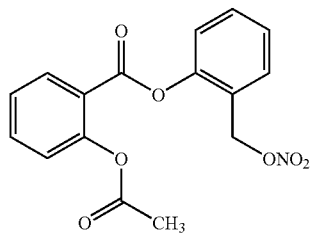

The 2-acetyloxybenzoic acid 2-(nitrooxymethyl)phenyl ester is synthesized according to the process described in Example 6, starting from acetylsalicylic acid and 2-hydroxybenzaldehyde. Total yield of the process 68%.

$^1$H NMR (CDCl$_3$): 8.22 (1H, dd); 7.68 (1H, dt); 7.35 (6H, m); 5.40 (2H, s); 2.30 (3H, s).

Pharmacological Examples

Example F1

Determination of the Capability of the Compounds of the Invention to Protect the Animals from the Liver Injury Induced by Concanavalin A.

The model in vivo used in the present example has been described in Tiegs G, Hentshel J, A Wendel. A T cell-dependent experimental liver injury in mice induced by Concanavalin A. J. Clin. Invest. 1992; 90:196-203.

The animals (rats of Swiss stock weighing about 20 g) are divided in groups of at least No. 10 animals for group. The animals receive concanavalin and solvent (treated control group), solvent (polyethylene glycol 400—untreated control group), concanavalin and tested compound dissolved in the solvent (treated groups).

Rats are treated intravenously with concanavalin A (0.3 mg/rat), and after 5 minutes they receive by intraperitoneal injection the tested compounds, at the doses reported in Table 1, dissolved in polyethylenglycol 400.

Eight hours after the concanavalin A injection all the animals were sacrificed and the blood collected and examined. The data, reported in Table 1, are expressed as value of the plasmatic glutamic-pyruvic transaminase percentage of the animals treated with the tested compound with respect to the animals of the treated control group.

The results show that the compounds according to the invention protect from the liver injury induced by concanavalin A, while the native or precursor compounds even worsen the liver injury.

Example F2

Determination of the Antiproliferative Activity of the Compounds of the Invention in Cancerous Cells.

Human adenocarcinoma (HT29) cells taken from colon affected by cancerous process were transferred into plates with 24 wells containing a cellular culture medium formed by 10% of foetal bovine serum, penicillin (50. U/ml), streptomycin (50 mg/ml) and PEG 400 (polyethylenglycol). After 24 hours a part of the plates is inoculated with the tested compounds dissolved in the carrier (PEG 400). 96 hours after the inoculation of the compounds the cellular growth was measured by haemocytometer. The results, reported in Table 2, are expressed as percentage of the cellular proliferation with respect to the controls.

The obtained results show that the compounds of the invention are much more effective in inhibiting the proliferation of the cancerous cells with respect to the corresponding native compounds.

Example F3

Determination of the Antiproliferative Activity of the Compounds of the Invention in Cancerous Epithelial Cells of Bladder and Prostate.

The experiment was carried out by using three human epithelial cellular lines of the prostate cancer (PNT1A; LLN-CaP; PC3) and three human epithelial cellular lines of the bladder cancer (T24; 647V; 1207), the various types of cellular lines are identified on the basis of the characteristics, in particular of the aggressiveness, of the cancerous process.

The cancerous cells are sown, with an initial concentration of 20,000 cells/cm$^2$, in plates having 96 wells with a cellular culture medium RPMI added with foetal bovine serum 5% and L-Glutamine 1%. Solutions in dimethylsulphoxide of the tested compounds at three different concentrations ($10^{-6}$ M; $10^{-5}$ M; $10^{-4}$M) or the carrier (DMSO 1‰) are added to the culture medium. 4 days after the treatment the cellular growth was measured by the method with MTT (3-[4,5-dimethylthiazol-2-yl]-2,5-diphenyltetrazolium bromide) de-scribed by Turner in: Turner T., Chen P., Goodly L. J., Wells A. Clin. Exp. Metastasis 1996, 14, 409-418. The results, reported in Table 3, are expressed as inhibition percentage of the cellular proliferation determined by measuring the cellular proliferation in the cellular cultures treated with the tested compounds with respect to that measured in cellular cultures treated with dimethylsulphoxide 1‰.

The results reported in Table 3 show that the nitrooxybutyl ester of sulindac (Ex. 18) at the $10^{-5}$ M concentration has a strong inhibitory effect on the proliferation of all kinds of cancerous cells examined; the compound of Ex. 16, reported in the Table with the simplified denomination of nitrooxybutyl ester of the ibuprofen der with ferulic ac. and the compound of Ex. 17, reported in the Table with the simplified denomination of nitrooxybutyl ester of the flurbiprofen der. with ferulic ac., are active in very aggressive prostate and bladder tumours, as it is shown by the results obtained on the cellular lines LNCaP and PC3, and 647V, 1207. The compound of Ex. 7, reported in the Table with the simplified denomination of nitrooxybutyl ester of the aspirin der. with ferulic ac. is active, at $10^{-5}$ concentrations, in prostate tumours as shown by the results obtained on the cellular lines LNCaP and PC3.

Example F4

Determination in Vitro of the Effect of the Compounds of the Invention on the Timidine Incorporation in Human Adeno-Carcinoma HT29 Cells.

Human adenocarcinoma cells are sown on plates having 24 wells (2.5×10$^5$ cells/plate) with a standard culture medium.

After 24 hours some plates are inoculated with the tested compounds dissolved in dimethylsulphoxide at a 200 μM concentration and others are treated with the tested compounds dissolved in dimethylsulphoxide at a 200 μM concentration in the presence of a solution of cisplatinum 25 μM.

After 15 hours of incubation the plates are put into contact with a solution of $^3$H-timidine 1 µCi/mol (RAS. 3,000 Ci/mol).

The cell monolayer of each plate is first washed twice with a cold saline buffer, then treated with TCA (trichloroacetic acid) at 5% for 10 minutes and then washed three times with absolute alcohol. The cells of each well are dissolved in 500 µl of NaOH 0.1N and the incorporated radioactivity is determined by scintallation counting.

The obtained results are reported in Table 4 and expressed as percentage of $^3$H-Timidine incorporated in the cells treated with the tested compounds and in the presence of Cisplatinum, considering equal to 100 the amount of $^3$H-Timidine incorporated in the cells treated only with Cisplatinum.

TABLE 1

Activity in the prevention of the liver injury induced by Concavalin A

| Treatment | Dose (mg/kg) | Liver injury % |
|---|---|---|
| Treated controls | — | 100 |
| Untreated controls | — | 2 |
| Paracetamol | 500 | 160 |
| Nitrooxybutyl ester of the Paracetamol der. with ferulic acid (Ex. 8) | 500 | 8 |
| Paracetamol nitrooxybutyl ester (Ex. 9) | 500 | 10 |
| Aspirin | 300 | 120 |
| Aspirin ester with 5-nitrooxymethyl-2-hydroxymethyl pyridine (Ex. 3) | 300 | 5 |
| Aspirin ester with 3-nitrooxymethyl-2-hydroxymethyl pyridine (Ex. 4) | 300 | 7 |
| Sulindac | 200 | 115 |
| Ester sulindac with 6-nitrooxymethyl-2-hydroxymethyl pyridine (Ex. 19) | 200 | 23 |
| Sulindac 4-nitrooxybutyl ester (Ex. 18) | 200 | 18 |

TABLE 2

Activity in vitro on the proliferation of cancerous cells

| Treatment | Concentration (µM) | Proliferation % |
|---|---|---|
| Controls | — | 100 |
| Aspirin | 500 | 100 |
| Nitrooxybutyl ester of the aspirin der. with ferulic acid (Ex. 7) | 300 | 50 |
| Aspirin ester with 3-nitrooxymethylphenol (Ex. 5) | 300 | 40 |
| Aspirin ester with 4-nitrooxymethylphenol (Ex. 6) | 10 | 0 |
| Aspirin ester with 6-nitrooxymethyl-2-hydroxymethyl pyridine (Ex. 1) | 10 | 0 |
| Aspirin ester with 2-nitrooxymethylphenol (Ex. 20) | 20 | 50 |
| Sulindac | 50 | 100 |
| Sulindac 4-nitrooxybutyl ester (Ex. 18) | 50 | 0 |

TABLE 3

Determination in vitro of the inhibitory effect on the proliferation of cancerous human cells of prostate cancer and of bladder cancer of the compounds of the invention

| | | Inhibition of the proliferative activity (%) | | | | | |
|---|---|---|---|---|---|---|---|
| | | Human epithelial cells of prostate cancer | | | Human epithelial cells of bladder cancer | | |
| Compounds | Conc. (M) | PNT1A | LNCaP | PC3 | T24 | 647V | 1207 |
| Sulindac | $10^{-6}$ | 3 | 17 | 5 | 0 | 9 | 0 |
| Nitrooxybutyl ester (Ex. 18) | $10^{-5}$ | 38 | 74 | 68 | 82 | 80 | 74 |
| | $10^{-4}$ | 81 | 88 | 74 | 93 | 92 | 88 |
| Nitrooxybutyl ester of the Ibuprofen der. with Ferulic acid (Ex. 16) | $10^{-6}$ | 0 | 8 | 4 | 0 | 0 | 2 |
| | $10^{-5}$ | 4 | 33 | 9 | 0 | 0 | 0 |
| | $10^{-4}$ | 20 | 60 | 47 | 22 | 45 | 43 |
| Nitrooxybutyl ester of the Flurbiprofen der. with Ferulic acid (Ex. 17) | $10^{-6}$ | 0 | 1 | 8 | 0 | 0 | 0 |
| | $10^{-5}$ | 2 | 26 | 20 | 0 | 13 | 0 |
| | $10^{-4}$ | 13 | 58 | 53 | 23 | 41 | 34 |
| Nitrooxybutyl ester of the aspirin der. With Ferulic acid (Ex. 7) | $10^{-6}$ | 0 | 20 | 1 | 2 | 0 | 4 |
| | $10^{-5}$ | 0 | 47 | 30 | 0 | 0 | 24 |
| | $10^{-4}$ | 72 | 81 | 69 | 55 | 50 | 82 |

TABLE 4

Determination in vitro of the effect of some compounds on the timidine incorporation in human adenocarcinoma cells

| Treatment | Conc. (µM) | Without Cisplatinum | With 25 µM Cisplatinum |
|---|---|---|---|
| Controls | — | 438 | 100 |
| Carrier (DMSO) | — | 438 | 100 |
| Salicylic acid Comparison | 200 | 438 | 100 |
| 3-(nitrooxymethyl) phenyl ester of Salicylic acid (Ex. 15) | 200 | 246 | 50 |
| Acetylsalicylic acid Comparison | 200 | 438 | 100 |
| 3-(nitrooxymethyl) phenyl ester of Acetylsalicylic acid (Ex. 5) | 200 | 192 | 46 |

The invention claimed is:

1. A compound having the following general formula (I):

$$A\text{-}X_1\text{-}L\text{-}(W)_p\text{-}NO_2 \quad (I)$$

wherein:
p is an integer equal to 1 or 0;
A=R-T$_1$-, wherein
R has the following formula:

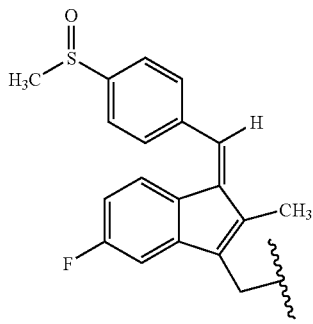

(AII)

$T_1$=(CO)$_t$ or (X)$_{t'}$, wherein X=O, S or NR$_{1C}$, wherein R$_{1C}$ is H or a linear or branched alkyl, having from 1 to 5 carbon atoms, t and t' are integers and equal to zero or 1, with the proviso that t=1 when t'=0; t=0 when t'=1;

$X_1$=-T$_B$-Y-T$_{B1}$- wherein
T$_B$ and T$_{B1}$ are equal or different;
T$_B$=(CO) when t=0, T$_B$-X when t'=0, X being as above;
T$_{B1}$=(CO)$_{tx}$, or (X)$_{txx}$, wherein tx and txx have the value of 0 or 1; with the proviso that tx=1 when txx=0; and tx=0 when txx=1; X is as above;

Y is selected from the following:

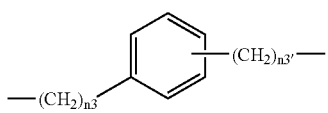

(III)

wherein n3 is an integer from 0 to 3 and n3' is an integer from 1 to 3;

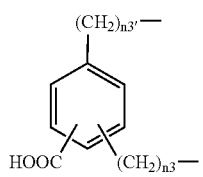

(IV)

wherein n3 and n3' have the above meaning, or

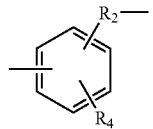

(V)

wherein
R$_4$ is hydroxy, hydrogen, or R$_5$O— alkoxy wherein R$_5$ is a C$_1$-C$_{10}$ linear, branched or cyclic alkyl group; and
R$_2$ is a C$_2$-C$_{10}$ linear or branched alkenylene group which can contain one or more double bonds,
L=covalent bond, CO or X, X being as defined above;
W=Y$_T$O wherein Y$_T$ has the same meanings of Y as defined above, and Y$_T$ is equal to or different from Y.

2. The compound of formula (I) according to claim 1, wherein Y is:

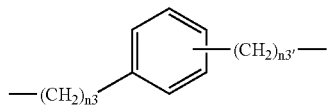

(III)

wherein n3 is an integer from 0 to 3 and n3' is an integer from 1 to 3.

3. A pharmaceutical formulation containing as active ingredient a compound of formula (I) according to claim 1 and a pharmaceutically acceptable excipient.

* * * * *